United States Patent [19]

Curro et al.

[11] Patent Number: 4,778,644

[45] Date of Patent: Oct. 18, 1988

[54] METHOD AND APPARATUS FOR MAKING SUBSTANTIALLY FLUID-IMPERVIOUS MICROBUBBLED POLYMERIC WEB USING HIGH PRESSURE LIQUID STREAM

[75] Inventors: John J. Curro; Donald L. Gerth; William I. Mullane, Jr., all of Cincinnati, Ohio

[73] Assignee: The Procter & Gamble Company, Cincinnati, Ohio

[21] Appl. No.: 88,930

[22] Filed: Aug. 24, 1987

[51] Int. Cl.⁴ .................. B29C 59/04; B29C 59/06; B29C 51/10; B29C 51/42
[52] U.S. Cl. .................................. 264/557; 264/280; 264/519; 264/570; 425/326.1; 425/328; 425/363; 425/384; 425/387.1; 425/388; 604/358; 604/372
[58] Field of Search ............... 264/557, 154, 280, 281, 264/282, 504, 519, 570; 604/378, 383, 385.1, 372, 358; 425/326.1, 328, 384, 387.1, 363, 388

[56] References Cited

U.S. PATENT DOCUMENTS

| | | |
|---|---|---|
| Re. 23,910 | 12/1954 | Smith et al. . |
| 2,045,384 | 6/1936 | Gerb . |
| 2,123,552 | 7/1938 | Helwig . |
| 2,660,757 | 12/1953 | Smith et al. . |
| 2,776,451 | 1/1957 | Chavannes . |
| 2,776,452 | 1/1957 | Chavannes . |
| 2,862,251 | 12/1958 | Kalwaites ............... 19/161 |
| 2,905,969 | 9/1959 | Gilbert et al. . |
| 3,038,198 | 6/1962 | Schaar . |
| 3,054,148 | 9/1962 | Zimmerli . |
| 3,084,389 | 4/1963 | Doyle . |
| 3,468,311 | 9/1969 | Gallagher ............... 128/296 |
| 3,484,835 | 12/1969 | Trounstine et al. . |
| 3,540,959 | 11/1970 | Connor ................ 156/203 |
| 3,560,601 | 2/1971 | Johnson et al. .......... 264/93 |
| 3,605,191 | 9/1971 | Kaspar . |
| 3,645,264 | 2/1972 | Gallagher ............... 128/296 |
| 3,654,047 | 4/1972 | Berkowitz . |
| 3,685,930 | 8/1972 | Davis et al. ............. 425/71 |
| 3,704,194 | 11/1972 | Harrier ................. 156/245 |
| 3,709,647 | 1/1973 | Barnhart ............... 425/224 |
| 3,724,673 | 4/1973 | Ryon .................. 210/500 |
| 3,760,940 | 9/1973 | Bustin ................. 206/58 |
| 3,814,101 | 6/1974 | Kozak ................. 128/287 |
| 3,862,282 | 1/1975 | Watson ................ 264/41 |
| 3,881,210 | 5/1975 | Drach et al. .......... 15/104.93 |
| 3,881,489 | 5/1975 | Hartwell ............... 128/287 |
| 3,881,491 | 5/1975 | Whyte ................. 128/287 |
| 3,911,187 | 10/1975 | Raley ................. 428/180 |
| 3,929,135 | 12/1975 | Thompson .............. 128/287 |
| 3,947,174 | 3/1976 | Hureau et al. ........... 425/72 |
| 3,957,414 | 5/1976 | Bussey, Jr. et al. ........ 425/384 |
| 3,966,383 | 6/1976 | Bussey, Jr. et al. ........ 425/388 |
| 3,989,867 | 11/1976 | Sisson ................. 428/132 |
| 4,132,594 | 1/1979 | Bank et al. ............. 195/1.8 |

(List continued on next page.)

*Attorney, Agent, or Firm*—E. Kelly Linman; John V. Gorman; Richard C. Witte

[57] ABSTRACT

A method for applying a high pressure liquid jet or stream to a web of polymeric film while the film is supported on a moving forming structure to produce a novel microbubbled substantially fluid-impervious web exhibiting substantially the same consumer preferred soft and silky tactile impression and reduced noise generation levels heretofore only achievable in microapertured, and hence substantially fluid pervious polymeric webs. In a particularly preferred embodiment, the microbubbled polymeric web exhibits a fine-scale pattern of discrete mushroom shaped surface aberrations, each of said surface aberrations having its amplitude oriented substantially perpendicular to the surface in which the surface aberration originates. Apparatus for producing microbubbled webs either in "planar" or "macroscopically expanded" form are also disclosed.

42 Claims, 15 Drawing Sheets

U.S. PATENT DOCUMENTS

| | | | |
|---|---|---|---|
| 4,151,240 | 4/1979 | Lucas et al. | 264/504 |
| 4,155,693 | 5/1979 | Raley | 425/363 |
| 4,192,699 | 3/1980 | Lewicki et al. | 156/145 |
| 4,226,828 | 10/1980 | Hall | 264/555 |
| 4,259,286 | 3/1981 | Louis et al. | 264/555 |
| 4,262,049 | 4/1981 | Kaspar | 428/131 |
| 4,272,473 | 6/1981 | Riemersma et al. | 264/154 |
| 4,280,978 | 7/1981 | Dannheim et al. | 264/156 |
| 4,303,609 | 12/1981 | Hureau et al. | 264/504 |
| 4,317,792 | 3/1982 | Raley et al. | 264/504 |
| 4,323,069 | 4/1982 | Ahr et al. | 128/287 |
| 4,327,730 | 5/1982 | Sorensen | 128/287 |
| 4,342,314 | 8/1982 | Radel et al. | 128/287 |
| 4,343,848 | 8/1982 | Leonard, Jr. | 428/156 |
| 4,351,784 | 9/1982 | Thomas et al. | 264/22 |
| 4,376,147 | 3/1983 | Byrne et al. | 428/167 |
| 4,395,215 | 7/1983 | Bishop | 425/290 |
| 4,463,045 | 7/1984 | Ahr et al. | 428/131 |
| 4,518,643 | 5/1985 | Francis | 428/131 |
| 4,546,029 | 10/1985 | Cancio et al. | 428/141 |
| 4,552,709 | 11/1985 | Koger, II et al. | 264/504 |
| 4,591,523 | 5/1986 | Thompson | 428/131 |
| 4,601,868 | 7/1986 | Radel et al. | 264/504 |
| 4,609,518 | 9/1986 | Curro et al. | 264/504 |
| 4,629,643 | 12/1986 | Curro et al. | 428/131 |
| 4,637,819 | 1/1987 | Ouellette et al. | 604/369 |
| 4,681,793 | 7/1987 | Linman et al. | 428/138 |
| 4,695,422 | 9/1987 | Curro et al. | 264/504 |

FOREIGN PATENT DOCUMENTS

| | | |
|---|---|---|
| 0059506 | 9/1982 | European Pat. Off. |
| 506599 | 9/1930 | Fed. Rep. of Germany |
| 1177324 | 9/1964 | Fed. Rep. of Germany |
| 2021479 | 12/1979 | United Kingdom |

*Primary Examiner*—Philip Anderson

METHOD AND APPARATUS FOR MAKING SUBSTANTIALLY FLUID-IMPERVIOUS MICROBUBBLED POLYMERIC WEB USING HIGH PRESSURE LIQUID STREAM

TECHNICAL FIELD

The present invention has relation to a substantially fluid-impervious, microbubbled polymeric web exhibiting reduced plastic "rattle" when subjected to movement and a cloth-like visual and tactile impression on at least one of its surfaces.

The present invention has further relation to such a fluid-impervious web exhibiting a fine scale pattern of discrete surface aberrations, each of said surface aberrations having its amplitude oriented substantially perpendicular to the surface in which said surface aberration originates. A small, highly flexible bubble (microbubble) comprised of material which has been substantially thinned, but not ruptured, is provided substantially coincidental with the point of maximum amplitude of each surface aberration. If the polymeric web is initially opaque, the degree of thinning normally produces transparency in the microbubbled portion of the surface aberration. The thinned microbubbled portion of the surface aberration prevents the transmission of liquids through the web, but enhances the web's permeability to gases and vapors.

The discontinuity created by the thinned, highly flexible bubble at the peak of each of the surface aberrations substantially reduces the resistance to both compression and shear of each individual surface aberration. In addition, the highly flexible, thinned membrane comprising the bubble wall permits the bubble to be easily deflected when relative movement with the user's skin occurs. Thus fluid-impervious microbubbled webs of the present invention exhibit a significantly improved tactile response over prior art fluid-impervious webs which are either embossed or surface textured, but which do not exhibit the degree of thinning achieved in the microbubble portion of webs of the present invention. In particular, the tactile response experienced when the user's skin contacts the pattern of highly flexible microbubbles in webs of the present invention is a much softer sensation than that experienced with webs employng similar fluid-impervious fine scale patterns of surface aberrations, but which do not include such microbubbles. This difference in tactile impression is most pronounced in shearing actions, i.e., when the web's contact with the skin involves lateral movement relative to the skin rather than simple compressive movement perpendicular to the skin.

In a preferred embodiment, microbubbled webs of the present invention can be macroscopically expanded into a three-dimensional configuration to impart a macroscopic pattern which is readily visible to the naked eye when the perpendicular distance between the plane of the web and the viewer's eye is about twelve inches.

In a particularly preferred embodiment, the present invention has relation to items of wearing apparel wherein the microbubbled webs are oriented so that the microbubbles are exposed and can contact the wearer's skin. When so oriented, the softness of the thinned microbubbles is often perceived as presenting a suede-like appearance and tactile impression, particularly when stroked laterally across the user's skin. In other situations where a low-friction exposed surface is desired, microbubbled webs of the present invention may be oriented so that the microbubbles do not contact the wearer's skin, e.g., if used as a diaper backsheet, the microbubbles could be oriented toward the absorbent core.

Regardless of which direction the microbubbles are oriented in use, the present invention has particular relation to substantially fluid-impervious microbubbled polymeric webs which are surprisingly "quiet" when subjected to movement, for example, when used as a substantially fluid-impervious backsheet in a disposable absorbent bandage such as an adult incontinent diaper or brief. In particular, it has been found that microbubbling of a given polymeric film in accordance with the present invention yields a significant reduction in the plastic "noise" generation capability of the original unbubbled film, i.e., fluid-impervious unembossed plastic webs of the prior art typically exhibit a distinct "rattling" or "rustling" sound when subjected to movement.

The present invention has further relation to microbubbled polymeric films which are much quieter than fluid-impervious embossed structures having similar patterns of fine scale surface aberrations, but which do not include microbubbles coincident with the maximum amplitude of their surface aberrations. Such a dramatic reduction in "noise" had previously been obtainable only by microaperturing the polymeric films, thereby making them fluid pervious. However, because of their inability to prevent fluid transmission, such "quiet" microapertured films are not by themselves well suited for use in environments where restraint of fluids is desired, e.g., as in a backsheet for a disposable absorbent bandage such as an adult incontinent diaper or brief.

Finally, the present invention has relation to method and apparatus for producing said microbubbled webs in either a planar or macroscopically expanded, three-dimensional configuration.

BACKGROUND ART

It has long been known in the disposable absorbent bandage art that it is extremely desirable to construct absorptive devices, such as disposable diapers, sanitary napkins, incontinent devices, absorbent wound dressings, and the like, presenting a soft, cloth-like surface feel to the user's skin at any anticipated points of contact, e.g., as fluid pervious topsheets and/or fluid-impervious backsheets.

While woven and non-woven fibrous webs are often employed in situations where fluid must be transmitted through the web because of their pleasant surface feel, polymeric webs comprised of plastic film have been shown to exhibit more desirable fluid transport and fluid restraining characteristics in many circumstances.

The use of fluid pervious polymeric webs as topsheets is well known in the art. For example, U.S. Pat. No. 3,814,101 issued to Kozak on June 4, 1974, suggests the use of a fluid pervious hydrophobic film provided with a plurality of valvular slits which restrict the reverse flow of liquid from the absorbent element of the device as a topsheet for a disposable absorbent bandage.

Commonly assigned U.S. Pat. No. 3,929,135 issued to Thompson on Dec. 30, 1975, discloses an exemplary prior art fluid pervious, macroscopically expanded three-dimensional topsheet comprised of liquid impermeable material, but provided with tapered capillaries, said capillaries having a base opening in the plane of the topsheet and an apex opening remote from the plane of the topsheet, said apex opening being in intimate contact with the absorbent pad utilized in the disposable absorbent bandage.

For the purpose of interpreting the present specification and claims, the term "macroscopically expanded", when used to describe three-dimensional plastic webs, ribbons and films of the present invention, refers to webs, ribbons and films which have been caused to conform to the surface of a three-dimensional forming structure so that both surfaces thereof exhibit a three-dimensional pattern of surface aberrations corresponding to the macroscopic cross-section of said forming structure, the surface aberrations comprising said pattern being individualy discernible to the normal naked eye when the perpendicular distance between the viewer's eye and the plane of the web is about 12 inches. Such macroscopically expanded webs, ribbons and films are typically caused to conform to the surface of said forming structure by embossing, i.e., when the forming structure exhibits a pattern comprised primarily of male projections, by debossing, i.e., when the forming structure exhibits a pattern comprised primarily of female capillary networks, or by extrusion of a resinous melt directly onto the surface of a forming structure of either type. Also for the purpose of interpreting the present specification and claims, the term "planar", when utilized herein to describe plastic webs, ribbons and films of the present invention, refers to the overall condition of the web, ribbon or film when viewed by the normal naked eye on a macroscopic scale. In this context "planar" webs, ribbons and films may include webs, ribbons and films having a fine scale, yet visible pattern of surface aberrations on one or both sides thereof, the surface aberrations comprising said visible pattern not being individually discernible to the normal naked eye when the perpendicular distance between the viewer's eye and the plane of the web is about 12 inches.

Macroscopically expanded polymeric webs employing features to reduce gloss and improve tactile impression are also disclosed in the prior art, as is the use of such webs as topsheets and/or backsheets in disposable absorbent bandages. For example, commonly assigned U.S. Pat. No. 4,327,730 issued to Sorensen on May 4, 1982 discloses a disposable diaper having a fluid pervious textured topsheet of thermoplastic material. The topsheet is macroscopically expanded and is provided with a multiplicity of nubbles across its surface. The nubbles do not substantially alter the macroscopic profile of the film, but do impart a more cloth-like tactile impression and reduced gloss to the film.

Another macroscopically expanded three-dimensional polymeric web exhibiting a substantially non-glossy visible surface and cloth-like tactile impression is disclosed in commonly assigned U.S. Pat. No. 4,463,045 issued to Ahr et al. on July 31, 1984. The visible surface of the macroscopically expanded three-dimensional polymeric web of Ahr et al. is preferably provided with a regularly spaced, microscopic pattern of surface aberrations, said pattern being too fine to be discernible by the normal naked eye when the perpendicular distance between the viewer's eye and the plane of the web is about 12 inches, but which pattern of surface aberrations is highly effective in substantially eliminating specular reflection of incident light. The non-glossy surface of the web exhibits substantially no planar areas which are large enough to inscribe a four (4) mil diameter circle. Said webs may be produced by means of a one-sided forming process wherein said surface aberrations are transmitted through the thickness of the web during processing or by means of a two-sided forming process wherein said surface aberrations are imposed directly onto the visible surface of the web. The surface aberrations may comprise either protuberances projecting generally outwardly from the surface of the web or depressions projecting generally inwardly from the surface of the web, e.g., the knuckle pattern of a fine woven wire embossing member. Macroscopically expanded three-dimensional polymeric webs of the type disclosed in the patent to Ahr et al. are often employed as alternatives for cloth and fiber structures which contact the wearer's skin.

The commonly assigned patent to Ahr et al. teaches the criteria which must be met with respect to the regularly spaced pattern of surface aberrations in order to diffusely reflect incident light and thereby eliminate gloss. It further teaches that in those situations where a more cloth-like or fiber-like tactile impression in the resultant macroscopically expanded three-dimensional plastic web is also desired, the surface aberrations in the web should preferably exhibit an average amplitude of at least about 0.2 mils (i.e., 0.0002 inches), and most preferably at least about 0.3 mils (i.e., 0.0003 inches). According to Ahr et al., a more cloth-like or fiber-like tactile impression is perceived in macroscopically expanded three-dimensional plastic webs which meet the aforementioned amplitude criteria whether the surface aberrations comprise protuberances or depressions due to the fact that in either case the surface of the web is divided into at least two distinct planes separated from one another by a distance of at least 0.2 mils (i.e., 0.0002 inches). Ahr et al. further teach that in the case of protuberances, it is the tops of the aberrations which contact the observer's skin, while in the case of depressions it is the substantially planar surface in which said aberrations originate which contacts the observer's skin. Because said division is carried out in a fine microscopic pattern, only the reduced area of contact with the uppermost surface of the web and not existence of the pattern is tactually perceived.

Because of the superior fluid and vapor handling characteristics which can be provided in polymeric webs of the aforementioned type and their inherent cost advantages when contrasted to woven and non-woven fibrous webs, considerable developmental effort has been expended by manufacturer's of disposable absorbent bandages to improve the consumer's reaction to placing polymeric webs in contact with the skin. Indeed, much technological progress has been made toward eliminating the negative consumer reaction to placing polymeric webs comprised of plastic film in contact with the user's skin, particularly in the context of a wearer-contacting topsheet. See, for example, commonly assigned U.S. Pat. No. 4,342,314 issued to Radel et al. on Aug. 3, 1982, the aforementioned commonly assigned U.S. Patent to Ahr et al. and commonly assigned U.S. Pat. No. 4,637,819 issued to Ouellette et al. on Jan. 20, 1987, all of said commonly assigned U.S. Patents being hereby incorporated herein by reference. By comparison, relatively little attention has been specifically focused on improving the characteristics of polymeric webs when they are used as a fluid-impervious backsheet in a disposable absorbent bandage structure.

U.S. Pat. No. 3,911,187 issued to Raley on Oct. 7, 1975 discloses a typical prior art fluid-impervious thermoplastic film used as a backsheet in structures such as disposable absorbent bandages, said film having a permanently embossed design which allegedly simulates woven fabric or cloth and which has edge curl resistance under machine stress. The embossed design is made up of latitudinally and longitudinally alternating hollow protuberances and depression on both sides of the film. The width of the protuberances at their base varies from about 5 mils to about 50 mils, most preferably from about 5 mils to about 20 mils. In the disclosed embodiment, the protuberances are comprised of a multiplicity of planar wall segments.

U.S. Pat. No. 4,343,848 issued to Leonard, Jr. on Aug. 10, 1982 discloses another prior art fluid-impervious embossed thermoplastic film used as a backsheet, said film being characterized in that one surface thereof is provided with a plurality of rows of protuberances having the shape of pyramids with square bases which extend perpendicular to both the longitudinal and the transverse axes of the film. The protuberances are joined at the edge of the bases by flat valley portions which intersect each other at right angles. It is alleged that the embossed film has a low coefficient of friction and increased embossed thickness. The protuberances in the disclosed embodiment preferably have a base from about 4 mils to about 10 mils and a height from about ½ mil to about 4 mils. In the disclosed embodiment, the pyramids are comprised of substantially planar wall segments.

U.S. Pat. No. 4,484,835 issued to Trounstine on Dec. 16, 1969 discloses still another prior art fluid-impervious plastic film which allegedly simulates a plain woven fabric or cloth and which has edge-curl resistance under machine stress. The film is characterized as possessing a series of raised bosses, separated by substantially perpendicularly intersecting longitudinal and lateral channel-like areas on the top side of the film, said channel-like areas being spaced apart about 0.010 inch to form a network of generally rectangular-shaped channels separating the raised bosses, said raised bosses protruding above the channel-like areas to a height in the range of about 0.003 to about 0.004 inches.

U.S. Pat. No. 3,724,673 issued to Ryon on Apr. 3, 1973 discloses still another textured thin polymeric membrane. In particular, Ryon discloses a polymeric film comprised of thermoplastic material and having a myriad of thermoplastically formed deformations in which the film which defines the deformations is at least in part thinner than the film between said deformations. The deformations prevent cohesion between adjacent membranes without causing a reduction in oxygen transport capability when a plurality of membranes are utilized in fluid exchange devices such as blood oxygenators and dialyzers.

U.S. Pat. No. 4,132,594 issued to Bank et al. on Jan. 2, 1979 disclose a gas diffusion liquid storage bag wherein a blood bag made of medical grade plastic is made with a multiplicity of regions thin enough to permit a desired rate of diffusion therethrough of $CO_2$, yet which has thick or otherwise sufficiently reinforced regions to provide handling strength for the bag.

From the foregoing it is clear that fluid-impervious polymeric webs are very well known in the art. It is also clear that many artisans have employed prior art fluid-impervious polymeric webs as backsheets on disposable absorbent garments such as diapers and incontinence devices.

However, a major disadvantage of the prior art fluid-impervious webs which have to this point been used as backsheets on such structures is that they are "noisy" when worn, i.e., "rattling" or "rustling" sounds caused by the wearer's body movements may betray the fact that the protective garment is being worn. While this is not often a concern where infant garments are involved, adult incontinence devices are now finding widespread acceptance amongst persons unable to control their normal bodily discharges. To individuals afflicted with this problem, the "rattling" or "rustling" sounds often generated by body movement when wearing garments employing such prior art liquid-impervious backsheets can be extremely embarrassing.

For many years it was believed that these "rattling" or "rustling" sounds were simply an inherent characteristic of polymeric webs. However, commonly assigned U.S. Pat. No. 4,629,643 issued to Curro et al. on Dec. 16, 1986 teaches a way of providing a plastic film which not only exhibits a highly desirable soft and silky tactile impression, but which, in addition, is extremely effective in reducing the "noises" which normally result when plastic webs are employed in disposable absorbent bandage structures. Unfortunately, plastic webs of the type disclosed in the aforementioned commonly assigned U.S. Patent to Curro et al. are microapertured, i.e., they exhibit a fine scale pattern of surface aberrations which end in volcano-like apertures at their points of maximum amplitude. They are not by themselves suitable for use as backsheets, since they are not impervious to fluid.

One solution to providing a backsheet which exhibits the highly desirable soft and silky tactile impression of microapertured webs of the type disclosed in the aforementioned commonly assigned U.S. Patent to Curro et al., yet which is impervious to the passage of fluid, is disclosed in the commonly assigned, allowed U.S. Patent Application of E. Kelly Linman, John Joseph Curro and Eugene Weinshenker, Ser. No. 740,084, filed on May 31, 1985 and entitled NON-OCCLUDING, LIQUID-IMPERVIOUS BACKSHEET FOR ABSORPTIVE DEVICES.

The latter commonly assigned U.S. Patent Application of Linman, Curro and Weinshenker discloses a backsheet comprising a combination of two layers. The first layer, which does not contact the wearer's skin, is preferably comprised of a fluid-impervious layer of polymeric film or the like. The second layer, which is also preferably comprised of a polymeric film, is pervious to both gas and fluid by virtue of a fine scale pattern of relatively small surface aberrations, each ending in a volcano-like aperture at its apex. The web comprising the second layer is preferably produced in accordance with the teachings of the aforementioend commonly assigned U.S. Pat. No. 4,629,643 to Curro et al. The second layer is preferably oriented so that the tiny volcano-like cusps of the surface aberrations constitute the exposed portion of the backsheet. This minimizes the surface area of the web in contact with the wearer's skin at any points of contact between the backsheet and the wearer's skin. In addition, the tiny apertures in the second layer substantially prevent occlusion of the wearer's skin by permitting air to circulate between the first fluid-impervious layer of the composite backsheet and the wearer's skin through the tiny apertures in the second layer. This effect is enhanced even further when the first microapertured layer is macroscopically expanded to enhance the amount of stand-off between the wearer's skin and the fluid-impervious first layer.

While the fluid-impervious composite backsheet disclosed in the commonly assigned U.S. Patent Application of Linman, Curro and Weinshenker does represent a significant advance over prior art single layer plastic backsheets in the areas of improved visual and tactile impression and avoidance of skin occlusion at points of contact between the backsheet and the wearer's skin, it normally increases the cost of products on which it is employed due to the fact it comprises two layers of material rather than one. In addition, it has been observed that while composite backsheets of the type disclosed in the commonly assigned U.S. Patent Application of Linman, Curro and Weinshenker are in most instances less "noisy" than prior art single layer plastic backsheets, they are still not as "quiet" as the microapertured webs disclosed in commonly assigned U.S. Pat. No. 4,629,623 to Curro et al. when the microapertured webs are employed by themselves.

OBJECTS OF THE INVENTION

Accordingly, it is an object of the present invention to provide a polymeric web which exhibits the highly desirable cloth-like visual and tactile impression of microapertured webs of the type disclosed in commonly assigned U.S. Pat. No. 4,629,643 to Curro et al., but which is substantially impervious to the passage of fluid.

It is another object of the present invention to provide such a substantially fluid-impervious polymeric web which exhibits low "noise" generation characteristics similar to those exhibited by said microapertured polymeric webs when said web is subjected to movement.

It is another object of the present invention to provide such a substantially fluid-impervious polymeric web which is suitable for use as a fluid retaining barrier in applications such as a backsheet for a disposable absorbent bandage.

It is still another object of the present invention to provide highly efficient method and apparatus for producing such substantially fluid-impervious polymeric webs at high speed and at relatively low cost.

DISCLOSURE OF THE INVENTION

The present invention, in a particularly preferred embodiment, comprises a substantially fluid-impervious, microbubbled polymeric web exhibiting low "noise" generation characteristics when subjected to movement, said web also exhibiting a soft and silky cloth-like visual and tactile impression on at least one of its surfaces. Prior to the present development, the consumer preferred attributes of soft and silky tactile impression and reduced "noise" generation were only attainable in plastic webs by providing the webs with a fine scale pattern of microapertures generally in accordance with the teachings of commonly assigned U.S. Pat. No. 4,629,643 to Curro et al., thereby making the webs substantially fluid pervious.

In particular, the present invention pertains to the provision of a substantially fluid-impervious microbubbled polymeric web exhibiting a fine scale pattern of discrete surface aberrations, each of said surface aberrations having its amplitude oriented substantially perpendicular to the surface in which the surface aberration originates. However, unlike the microapertured web disclosed in commonly assigned U.S. Pat. No. 4,629,643 to Curro et al., at least one tiny, continuous membrane bubble, i.e., a microbubble, is provided substantially coincidental with the maximum amplitude of each surface aberration. Thus, microbubbled webs of the present invention are substantially fluid-impervious.

Microbubbled webs of the present invention are also structurally distinct from prior art fluid-impervious embossed and/or surface textured webs of the type described in the BACKGROUND ART portion of the present specification. In particular, while the prior art embossed and/or surface textured webs cited earlier herein may exhibit a slight thinning of the web at the points of embossment or surface texturing, the surface aberrations present in microbubbled webs of the present invention include at their points of maximum amplitude at least one continuous membrane which is very much thinner than the base portion of the surface aberration in which the microbubble originates. Unlike the embossments and points of surface texturing in prior art fluid-impervious plastic webs, the degree of thinning in the microbubbled portion of webs of the present invention is sufficient to substantially remove the stiffness from the affected portion of the surface aberration, thereby converting it into a thin, compliant, easily deformable membrane. In most instances, if the plastic web employed to produce a microbubbled web of the present invention is initially opaque, the degree of thinning is sufficient to produce translucency and, in many instances, transparency in the microbubbled portions of the surface aberrations. In addition, the maximum cross-sectional area of the thinned membrane portion of each microbubble is normally greater than the minimum cross-sectional area of the base portion of the surface aberration from which the microbubble originates, as measured in a set of parallel planes oriented perpendicular to the amplitude of the surface aberration. This produces a surface aberration having a mushroom-like appearance or shape when viewed from a side elevation.

While not wishing to be bound, it is believed that removing the stiffness from the microbubbled portion of each surface aberration provides a multiplicity of hinges or flex points throughout the web. As a result, microbubbled webs of the present invention are substantially less stiff than otherwise identical embossed webs which do not exhibit microbubbles at the tips of their embossments. Furthermore, the highly thinned and flexible membranes comprising the microbubbles are not able to couple mechanical motions induced in the web to the surrounding air. As a result, sound generation, which depends largely upon the degree of coupling, is significantly less than for otherwise identical embossed webs which do not exhibit highly thinned microbubbles at the tips of their embossments.

Unlike the microscopic pattern of surface aberrations disclosed in commonly assigned U.S. Pat. No. 4,463,045 to Ahr et al., the pattern of microbubbled surface aberrations provided in webs of the present invention, taken as a whole, may be visible to the normal naked eye at a perpendicular distance of about 12 inches. However, despite the visibility of the pattern, the microbubbled surface aberrations comprising the pattern are not individually discernible to the normal naked eye when the perpendicular distance between the viewer's eye and the plane of the web is at least about 12 inches. In this regard, it has been determined that individual microbubbled surface aberrations employed in webs of the present invention preferably have a maximum cross-sectional dimension of about 25 mils (0.025 inches) or less, most preferably about 15 mils (0.015 inches) or less, as measured in a plane oriented perpendicluar to the amplitude of the surface aberration to satisfy the foregoing individual discernibility criteria.

With respect to spacing of the microbubbled surface aberrations employed in webs of the present invention relative to one another, it has been determined that the distance between any given microbubbled surface aberration and an adjacent microbubbled surface aberration should preferably not exceed about 25 mils (0.025 inches), center-to-center, in any given direction.

The density of fine-scale microbubbled surface aberrations employed in webs of the present invention is preferably at least about 2,500 surface aberrations per square inch, as measured in an area which contains the aforementioned treatment. In this regard it should be noted that it is not a requirement that the entire surface of the web contain the pattern of microbubbled surface aberrations nor that the web be "planar" as that term is defined earlier herein, i.e., microbubbled webs of the present invention may, if desired, be macroscopically expanded to exhibit three-dimensional patterns such as those disclosed in commonly assigned U.S. Pat. Nos. 4,342,314 to Radel et al., 4,463,045 to Ahr et al., 4,637,819 to Ouellette et al. or U.S. Pat. No. 4,609,518 to Curro et al., all of the foregoing U.S. Patents being hereby incorporated herein by reference.

Furthermore, microbubbled surface aberrations may be employed on those portions of a web which are intended to remain substantially fluid-impervious, while other portions of the web may be microapertured to provide a web which exhibits a substantially uniform appearance and tactile impression, but which is pervious to fluid only in certain predetermined locations.

While it is not a requirement that the microbubbled surface aberrations employed on polymeric webs of the present invention be of the same size or that they form a regulated pattern, in a particularly preferred embodiment microbubbled webs of the present invention may be produced by impinging a jet of high pressure liquid on the exposed surface of a web of flat polymeric film while the film is supported on a first relatively fine mesh woven wire support member. The high pressure liquid jet causes the initially smooth flat film to assume the overall knuckle pattern of the first woven wire support member. A second much finer mesh porous support member preferably underlies the first woven wire support member. When it is at the correct depth, the second finer mesh porous support member underlying the first support member prevents the vast majority of highly thinned membranes formed at the tips of the surface aberrations from bursting while they are subject to the influence of the high pressure liquid jet. The result is a regulated pattern of fine scale bubbling, i.e., microbubbled surface aberrations are formed in those portions of the web coinciding with the interstices formed between the intersecting woven wire filaments comprising the first support member.

Thus, upon removal of the microbubbled web from the two-layer forming structure, the vast majority of surface aberrations corresponding to the interstices between the intersecting woven wire filaments on the first woven wire support member each exhibit at least one tiny unapertured bubble, i.e., a thinned microbubble, substantially coincidental with its point of maximum amplitude.

When using a first woven wire support structure of the aforementioned type, filaments having a diameter of about 9 mils (0.009 inches) and a mesh count of at least about 50 filaments per lineal inch by about 50 filaments per lineal inch have been found to produce "planar" microbubbled webs exhibiting a soft and silky visual and tactile impression as well as substantial imperviousness to fluids. Woven wire support members having at least about 80 filaments per lineal inch by about 80 filaments per lineal inch are particularly preferred for the first woven wire support member.

In an alternative process embodiment, "planar" microbubbled webs of the present invention can be produced utilizing a rotating cylindrical support structure having a fine scale pattern of female capillary networks to support a web of flat polymeric film as the film is passed through a pressure nip formed between the rotating cylindrical support member and a fluid laden porous rubber roll, preferably while the web is at an elevated temperature. In the latter process embodiment, the water carried by the porous rubber roll is pressurized as the rubber comprising the roll deforms in the pressure nip, thereby hydraulically forcing the unsupported portions of the film into the capillary networks existing in the support member. The pressurized fluid deforming the film into the capillary networks thereby thins the tip of each surface aberration formed in each capillary network to create a microbubble of the type described earlier herein.

As with microbubbled webs of the present invention produced via the high pressure liquid jet process, the maximum cross-sectional area of the thinned membrane portion of each resultant microbubble produced using the porous rubber roll process is normally greater than the minimum cross-sectional area of the base portion of the surface aberration in which the microbubble originates, as measured in a pair of parallel planes oriented perpendicular to the amplitude of the surface aberration. This is again believed to be due to the fact that the thicker base portion of the surface aberration exhibits a higher degree of elastic recovery than the highly thinned, plastically deformed microbubbled portion of the surface aberration.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

While the present invention will be described in the context of providing a "quiet", substantially fluid-impervious plastic backsheet for a disposable diaper exhibiting cloth-like visual and tactile impression on its exposed surface, the present invention is in no way limited to such application. The present invention may in fact be practiced to great advantage in any situation where a polymeric web exhibiting the following characteristics is required; (a) a barrier to fluid transmission; (b) cloth-like visual and tactile impression; and (c) minimal "noise" when the web is subjected to movement. The detailed description contained herein, which relates to a preferred structure and its use as a backsheet in a disposable diaper, will allow one skilled in the art to readily adapt the invention to other devices.

Figure 1:
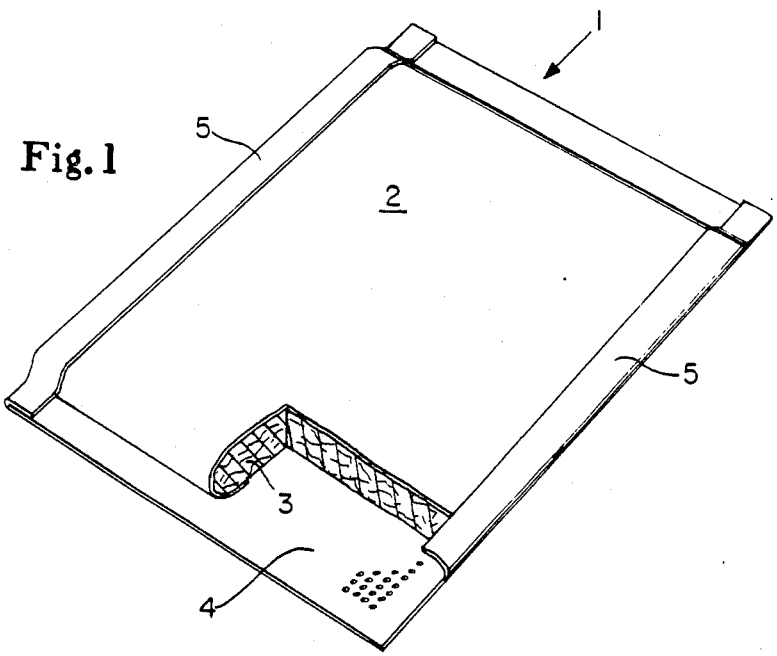
FIG. 1 is a simplified perspective representation, viewed from the topsheet side, of an unfolded disposable diaper employing a web of the present invention as a fluidimpervious backsheet, said diaper having portions of its components cut away for clarity.

FIG. 1 is a simplified perspective view of a disposable absorbent bandage comprising a diaper in an unfolded condition. Various layers have been cut away to more clearly show the structural details of this embodiment. The disposable diaper is referred to generally by the reference numeral 1. A fluid pervious topsheet is shown as 2. The other two major components of the disposable diaper 1 are the absorbent element or pad 3 and the fluid-impervious backsheet 4 of the present invention. In general, the side flaps 5 of the backsheet 4 are folded up so as to cover the edges of the absorbent pad 3 and topsheet 2. Topsheet 2 is generally folded to completely enclose the ends of the absorbent pad 3. As will be appreciated by those skilled in the art, the drawing of disposable diaper 1 in FIG. 1 is a simplified representation. A more detailed description of a preferred embodiment of a disposable diaper is contained in commonly assigned U.S. Pat. No. 3,952,745 issued to Duncan on Apr. 27, 1976, said patent being hereby incorporated herein by reference. As will also be appreciated by those skilled in the art, the topsheet 2 of the disposable diaper 1 show in FIG. 1 is normally oriented so as to contact the wearer's body in use, i.e., the topsheet side is considered to be the wearer contacting surface of the diaper.

Figure 2:
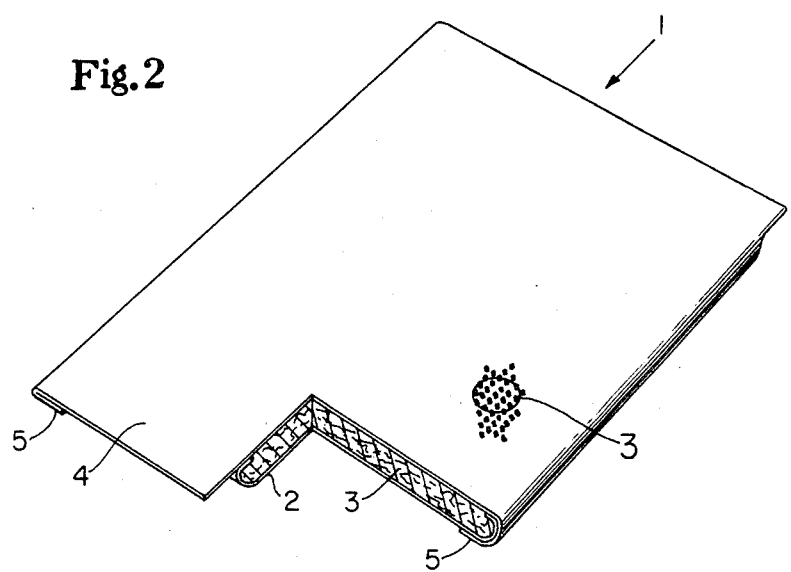
FIG. 2 is a simplified perspective representation of the unfolded disposable diaper of FIG. 1 viewed from the backsheet side thereof.

FIG. 2 is a perspective view of the disposable diaper 1 generally shown in FIG. 1 taken from the non-wearer contacting or backsheet surface thereof. Although it is clear that there will be some contact with the wearer's skin by the overlapping side flaps 5 of the backsheet, the bulk of the exposed area of the backsheet 4 is outwardly directed away from the wearer's skin in use. Accordingly, most contact between the exposed surface of the backsheet 4 and the wearer's skin will be made when the diaper 1 is being applied to the torso of the wearer. In the case of an infant diaper, the contact will most likely be with the hands of the person applying the diaper or holding the infant, while in the case of an adult incontinent diaper, the contact during application will most likely be with the hands of the wearer. In either case, it is generally desirable that the visual and tactile impression of the exposed surface of the backsheet 4 be as pleasant as possible. In most instances, a cloth-like visual and tactile impression are perceived as desirable, particularly when there is lateral movement between the user's skin and the backsheet.

Another highly desirable attribute for a fluid-impervious backsheet in a disposable absorbent bandage is that the web not make "rattling" or "rustling" sounds when subjected to movement, since structures which are made of cloth are normally very compliant and do not make "rattling" or "rustling" noises when subjected to movement. The latter characteristic is particularly important when fluid-impervious webs are employed in adult incontinent devices, since the "rustling" or "rattling" noises often generated by body movement when wearing garments employing prior art fluid-impervious backsheets can be extremely embarrasing to the user.

Figure 3:
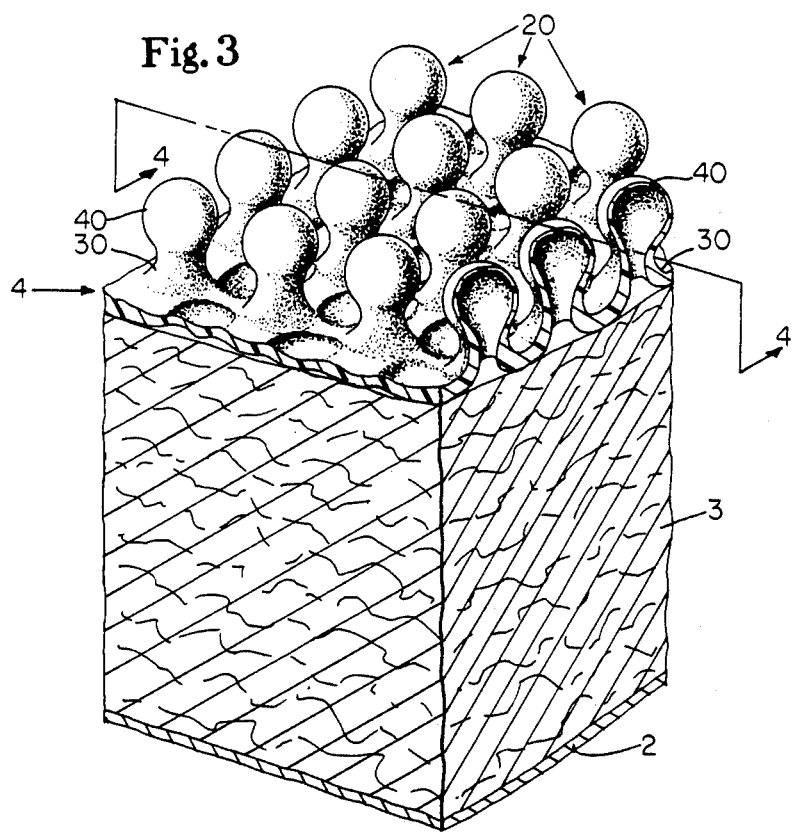
FIG. 3 is an illustration of a greatly enlarged segment of the diaper shown in FIG. 2 taken at a point corresponding to inset 3 in FIG. 2.

FIG. 3 is a greatly enlarged segment of the disposable diaper shown in FIGS. 1 and 2, said diaper employing a fluid-impervious "quiet" backsheet 4 of the present invention. The backsheet 4 shown in FIG. 3 exhibits a highly desirable cloth-like visual and tactile impression closely resembling that of a suede material.

Figure 4:
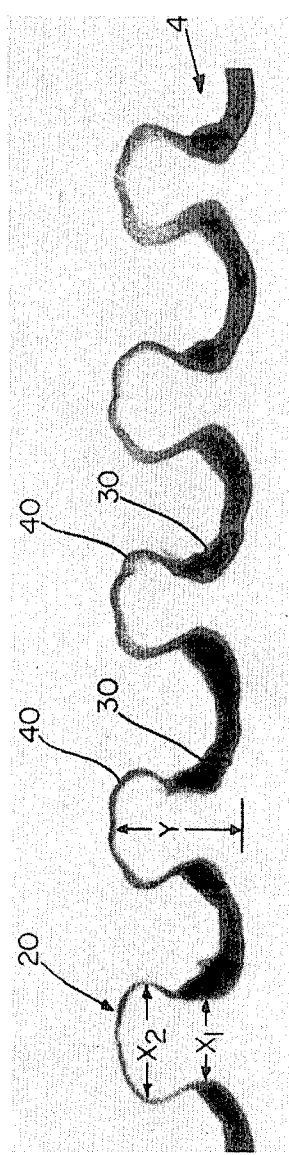
FIG. 4 is a highly enlarged cross-sectional photograph of an actual embodiment of a "planar" fluid-impervious web of the present invention taken at a point which would correspond to section line 4—4 of FIG. 3.

FIG. 4 is a highly enlarged photographic cross-section of an actual sample of a backsheet 4 of the type illustrated in FIG. 3, said cross-section being representative of what would be observed if the section were taken at a point corresponding to section line 4-4 in Figure 3. The "quiet" backsheet segment shown generally in Figures 3 and 4 exhibits a pattern of discrete surface aberrations 20, each having a base portion 30 and a thinned microbubbled portion 40 located at the point coinciding with the maximum amplitude of each surface aberration 20.

The backsheet 4 generally shown in FIG. 3 comprises a "planar" microbubbled web of the present invention, since the surface aberrations 20 are not individually discernible to the normal naked eye, i.e., a normal eye having 20/20 vision unaided by any instrument that changes the apparent size or distance of an object or otherwise alters the visual powers of the eye, when the perpendicular distance between the viewer's eye and the plane of the web is about 12 inches. The fact that the pattern formed by the surface aberrations 20, taken as a whole, may be discernible at this distance does not automatically remove the web from the "planar" category. In order to satisfy the foregoing individual indiscernibility criteria, individual microbubbled surface aberrations employed in substantially fluid-impervious webs of the present invention preferably exhibit a maximum cross-sectional dimension of about 25 mils (0.025 inches) or less, most preferably about 15 mils (0.015 inches) or less, as measured in a plane oriented perpendicular to the amplitude of the surface aberration with the microbubble in its fully expanded condition. By "fully expanded condition", it is meant that the microbubble has been expanded to its maximum volume, as by the introduction of a very slight fluid pressure inside the surface aberration.

With respect to spacing of the microbubbled surface aberrations 20 relative to one another, it has been determined that the distance between any given microbubbled surface aberration 20 and any adjacent microbubbled surface aberration 20 should preferably not exceed about 25 mils (0.025 inches), center-to-center, in any given direction.

The density of fine-scale microbubbled surface aberrations 20 employed in "quiet" substantially fluid-impervious webs of the present invention is preferably at least about 2,500 aberrations per square inch, as measured in any area of the web where improved visual and tactile impression and reduced "noise" are desired. In this regard it should be noted that the pattern, size and spacing of microbubbled surface aberrations of the present invention may be uniform or non-uniform, as desired, so long as the foregoing size and density criteria are generally satisfied.

As noted earlier herein, FIG. 4 is a greatly enlarged photograph of a "quiet" microbubbled web 4 of the present invention taken at a point which would generally correspond with section line 4—4 of Drawing FIG. 3. The cross-section of FIG. 4 shows only the fluid-impervious backsheet 4 of the diaper generally illustrated in Drawing FIG. 3, exclusive of the absorbent core element 3 and topsheet 2. As should be readily apparent from both the illustration of FIG. 3 and the photograph of FIG. 4, the microbubbled portion 40 of each surface aberration 20 comprises a relatively thin, continuous membrane secured about its periphery to a relatively thicker base portion 30 originating in the plane of the backsheet 4. Unlike prior art fluid-impervious embossed webs, the degree of thinning in the microbubbled portion 40 of webs of the present invention is sufficient to substantially remove the stiffness from the affected portion of the surface aberration 20, effectively converting it to a thin, compliant, easily deformable membrane. In the event the web of starting material is opaque, the degree of thinning is normally sufficient to render the microbubbled portion of the surface aberration substantially transparent.

As will also be apparent from Drawing FIGS. 3 and 4, the maximum internal cross-sectional area of the thinned membrane portion comprising each microbubble 40 (as measured in plane $X_2$ in FIG. 4) is greater than the minimum internal cross-sectional area (as measured in plane $X_1$ in FIG. 4) of the relatively thicker base portion 30 of the surface aberration 20 from which the microbubble originates. These measurements are made in a pair of parallel planes oriented perpendicular to the amplitude or axis of the surface aberration (as represented by Y in FIG. 4) with the microbubble in its fully expanded condition. Surprisingly, this latter phenomenon has been observed even on microbubbled webs produced with forming structures which employ substantially straight sidewalls to form the surface aberrations.

While not wishing to be bound, it is believed that the latter phenomenon is due primarily to the plastic yielding which takes place in the microbubbled portion 40 of the surface aberration relative to the more elastic deformation which takes place in the base portion 30 of the surface aberration. Once plastic deformation in the microbubbled portion 40 has occurred, there is little if any tendency toward elastic recovery, i.e., shrinking of the microbubbled portion of the surface aberration. By way of contrast, there is relatively less plastic deformation occurring in the base portion 30 of the surface aberration. Accordingly, once the forces causing deformation of the base portion 30 are removed the base portion undergoes at least a degree of elastic recovery, while the plastically deformed microbubbled portion 40 joined thereto does not. As a result, the minimum internal cross-sectional area of the thicker base portion 30 of the surface aberration, as measured in a plane approximately coinciding with the point at which the base portion 30 is joined to the microbubbled portion 40 of the surface aberration (e.g., plane $X_1$ in FIG. 4), is typically smaller than the maximum internal cross-sectional area of the fully expanded microbubbled portion 40, as measured in a parallel plane (e.g., plane $X_2$ in FIG. 4) located along the amplitude or axis Y of the surface aberration. Thus, microbubbled surface aberrations of the present invention normally exhibit a mushroom-like cross-sectional appearance or shape when viewed from a side elevation.

By way of contrast, embossed fluid-impervious plastic webs of the prior art do not exhibit either the degree of thinning at the ends of their embossments nor the mushroom-like cross-sectional appearance of microbubbled webs of the present invention. As a result, the prior art webs are not as "quiet", nor do they exhibit the same cloth-like visual and tactile impression of webs of the present invention.

Figure 5:
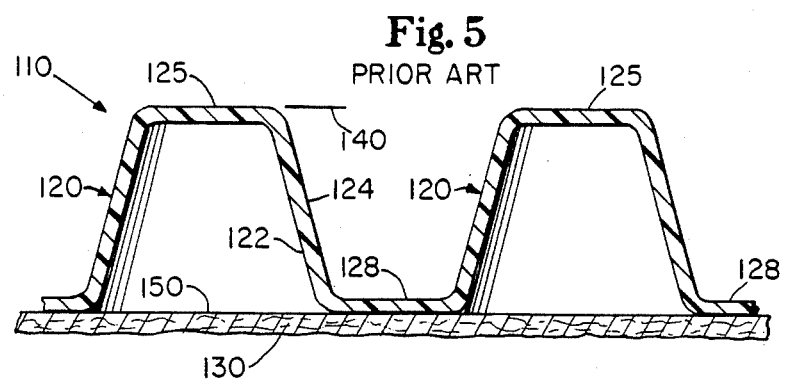
FIG. 5 is a simplified cross-sectional illustration of a "planar" prior art embossed web.

FIG. 5 is a greatly enlarged simplified cross-sectional view of a segment of an embossed, but nonetheless "planar", fluid-impervious prior art polymeric web 110 exhibiting a fine-scale pattern of surface aberrations 120. If desired, the surface aberrations 120 can be in accordance with the size and spacing criteria taught by the aforementioned commonly assigned U.S. Pat. No. 4,463,045 to Ahr et al., which is hereby incorporated herein by reference.

The prior art web 110 is shown at rest on a substrate 130 which may, if desired, comprise an absorbent element of a disposable absorbent bandage. In accordance with the teachings of the aforementioned commonly assigned U.S. Patent to Ahr et al., the overall caliper of the surface aberrations 120, i.e., the distance separating uppermost plane 140 and lowermost plane 150 is preferably at least about 0.2 mils (i.e., 0.0002 inches), and most preferably at least about 0.3 mils (i.e., 0.0003 inches).

According to the teachings of the commonly assigned U.S. Patent to Ahr et al., the fine scale pattern of surface aberrations 120 is effective in substantially eliminating specular reflection of incident light. The surface aberrations 120 may, if desired, correspond to the interstices between intersecting filaments of a woven wire support member on which the web is subjected to suction while in a heated condition. The valleys 128 intermediate adjacent surface aberrations 120 follow the contour of the filaments which support the web 110 while it is subjected to suction at an elevated temperature. Because the interstices between intersecting filaments in the woven wire support member are physically very tiny, the web 110 is caused to conform to the surface profile of the woven wire support member when subjected to vacuum. However, the vacuum is normally insufficient to aperture the web at the points coinciding with the relatively small unsupported interstices. Accordingly, the surface aberrations 120 exhibit a closed end wall 125 which is secured about its periphery to the sidewalls of the surface aberration. However, the degree of thinning of the end walls 125 does not approach that of microbubbled webs of the present invention. Accordingly, there are no membrane-like portions at the ends of prior art surface aberrations 120.

Figure 6:
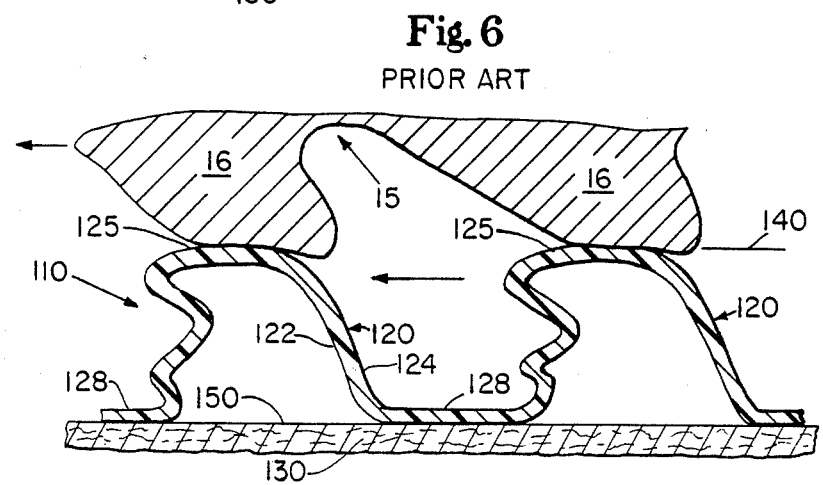
FIG. 6 is a simplified cross-sectional view of the "planar" prior art web shown in FIG. 5 illustrating the manner in which the embossments in the prior art web tend to deflect the papillary ridges in the skin of an observer's finger as it is stroked across the surface of the embossments.

FIG. 6 is a view of the prior art web 110 generally shown in FIG. 5 as it is subjected to a stroking action oriented generally parallel to the surface of the web. The papillary ridges on the skin 15 of the observer's finger are designated 16. As can be seen in FIG. 6, lateral stroking of the web's uppermost surface 124 by a portion of the papillary ridges 16 on the skin of the observer's finger causes the individual surface aberrations 120 to lean generally in the direction of travel of the contacting portion of the observer's finger, while the papillary ridges 16 on the observer's skin are deflected in a direction opposite the direction of travel. Note, also, that the closed end wall 125 of each surface aberration 120 tends to keep the side walls of each surface aberration to which it is secured about its periphery behaving as a discrete structural unit. While not wishing to be bound, it is believed that this behavior is much like that of an "arch" to which the side walls of a building are secured, i.e., the presence of the integral end wall 125 structurally reinforces the continuous side wall of each discrete surface aberration, thereby enhancing its resistance both to collapse and shear. Accordingly, it increases the deflection of the papillary ridges 16 of the skin 15 on the observer's finger.

Under relatively light pressures the papillary ridges 16 on the skin of the observer's finger contact only a limited portion of each surface aberration 120 as they move laterally across the surface of the web. Nonetheless, it is believed that the aforementioned reinforcing effect of the end walls 125 of each surface aberration tends to impart a resistance to deflection and collapse which detracts from the softness impression experienced by the user's skin. This resistance causes significant deflection of the papillary ridges 16 of the observer's skin 15 which in turn enhances the discernibility of the tactile pattern as the observer's finger moves laterally across the web's surface. This effect can be observed in the cross-section of FIG. 6.

Figure 7:
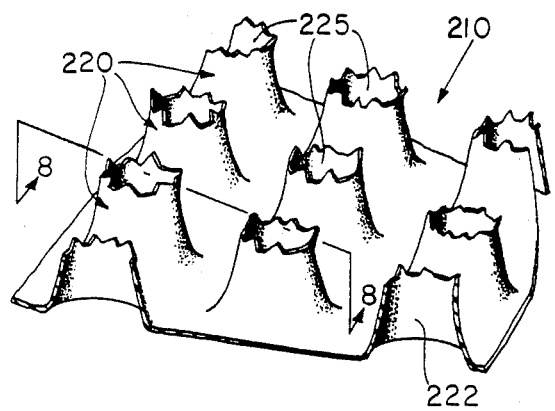
FIG. 7 is a simplified perspective illustration of a fluid pervious "planar" microapertured web of the type generally disclosed in commonly assigned U.S. Pat. No. 4,629,643 issued to Curro et al. on Dec. 16, 1986.

FIG. 7 is a greatly enlarged simplified perspective illustration of a microapertured web 210 of the type generally disclosed in commonly assigned U.S. Pat. No. 4,629,643 issued to Curro et al. on Dec. 16, 1986 and incorporated herein by reference. The microapertured web 210 exhibits a pattern generally similar to that of the unapertured prior art "planar" web 110. It may, if desired, be formed on a woven wire support member identical to that employed during formation of prior art "planar" web 110. However, rather than relying upon suction to fully conform the web to the surface of the woven wire support member, a high pressure liquid jet is preferably utilized for this purpose. Because of the greater driving force applied by the liquid jet, those portions of the web which coincide with the interstices formed between the intersecting filaments in the woven wire support member are not only deformed, but also thinned and ruptured to form tiny apertures, i.e., microapertures 225, at points which substantially coincide with the maximum amplitude of each surface aberration 220.

Figure 8:
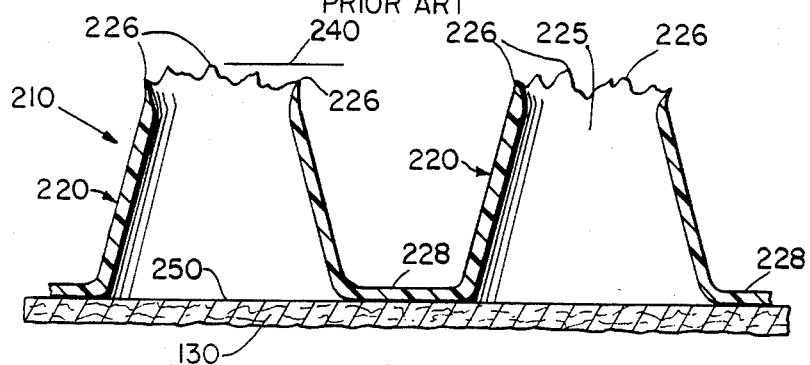
FIG. 8 is a simplified cross-sectional illustration of the "planar" microapertured web generally disclosed in FIG. 7 taken along section line 8—8 of FIG. 7.

As can be seen in the greatly enlarged cross-section of FIG. 8, rupturing of the surface aberrations 220 at these points results in the formation of a volcano-shaped aperture 225 having relatively thin, irregularly shaped petals 226 about its periphery. As can also be observed from FIG. 8, the outermost extremities of the petals 226 are substantially thinned due to the elongation which occurs just prior to rupture of the film by the high pressure liquid jet. If identically sized and patterned support structures are used to form both webs, the overall no-load caliper, i.e. the distance between uppermost plane 240 and lowermost plane 250 of "planar" microapertured web 210 is slightly greater than the overall no-load caliper of the unapertured prior art "planar" web 110 shown in FIG. 5 due to the drawing and thinning which takes place in the end wall of each surface aberration 220 immediately prior to rupture.

According to the teachings of the aforementioned commonly assigned U.S. Patent to Curro et al., the existence of the microapertures 225 is of much greater importance to the reduced "noise" and improved visual and tactile impression of microapertured web 210 than the size of the microapertures, i.e., the microaperture on the surface aberration reduces its overall resistance to compression and shear and destroys the ability of the surface aberration to respond as an integral reinforced unit.

Figure 9:
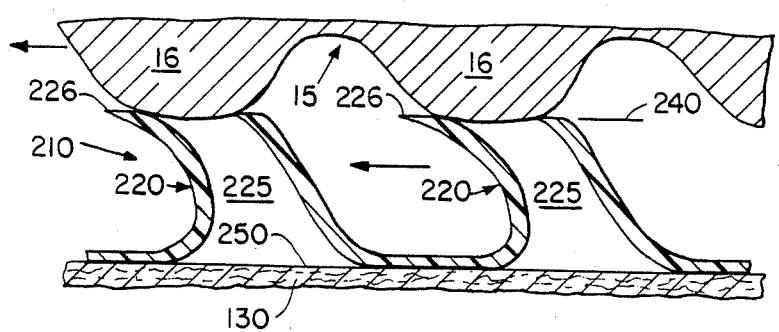
FIG. 9 is a simplified cross-sectional view of the "planar" web generally shown in FIG. 8 illustrating the behavior of the thinned, volcano-like apertures located at the peaks of the surface aberrations when laterally stroked by the papillary ridges on the skin of an observer's finger.

FIG. 9 is a greatly enlarged simplified illustration generally similar to that of FIG. 6, but showing the response of the prior art microapertured web 210 and the papillary ridges 16 on the skin 15 of the observer's finger when the observer's finger is moved laterally across the surface of the microapertures surface aberrations 220. The overall degree of collapse, i.e., the physical distance between uppermost plane 240 and lowermost plane 250, although initially somewhat greater than that of the prior art unapertured "planar" embossed web 110 shown in FIG. 5, is reduced to a level less than that for the prior art embossed web 110 shown in FIG. 6 for a comparable loading. Furthermore, because of the irregular and pliable nature of the thinned petals 226 formed about the periphery of microapertures 225, the papillary ridges 16 on the observer's skin 15 are not deflected as much as for the prior art embossed web shown in FIG. 6 when subjected to lateral stroking.

According to the teachings of the aforementioned commonly assigned U.S. Patent to Curro et al., all of the foregoing factors contribute to the user perception that the tactile response of the microapertured polymeric "planar" web 210 is substantially softer and silkier than that of the identically patterned embossed, but unapertured, web 110.

Figure 10:
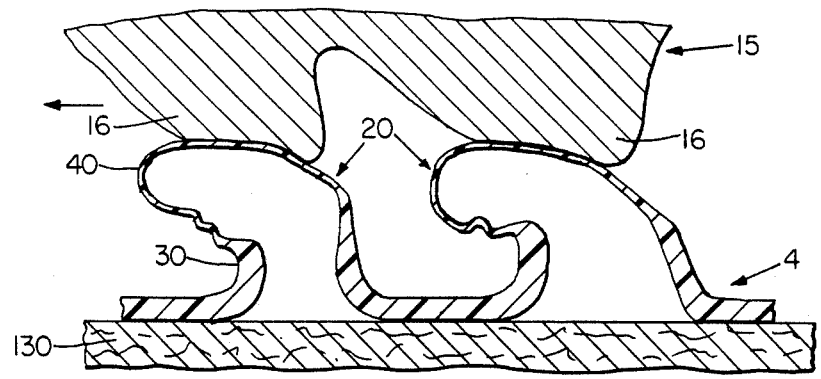
FIG. 10 is a simplified cross-sectional illustration of a "planar" web of the present invention, as generally shown in FIG. 3, illustrating the behavior of the microbubbles located at the point of maximum amplitude of the surface aberrations when laterally stroked by the papillary ridges on the skin of an observer's finger.

FIG. 10 is a greatly enlarged cross-sectional illustration generally similar to those of FIGS. 6 and 9, but illustrating the interaction between a "planar" microbubbled web 4 of the type generally shown in FIG. 3 and the papillary ridges 16 of the skin 15 on the observer's finger when the observer's finger is moved laterally across the surface of the microbubbled surface aberrations 20 under comparable loading conditions. In particular, note that the greatest degree of vertical collapse exhibited by the web 4 takes place mostly in the microbubbled portions 40 of the surface aberrations 20, while the base portions 30 undergo a much lesser degree of compression and/or deflection. Like the microapertures 225 in the web 210 of Curro et al., it is believed that the relatively thin membranes comprising the microbubbles 40 eliminate the "arch" effect present in the prior art embossed web 110 shown in FIGS. 5 and 6. Elimination of the "arch" effect permits the sidewalls of each of the surface aberrations 20 to undergo a greater degree of flexing under comparable loadings. In addition, the resistance to collapse or deformation of the microbubbled portion 40 of each surface aberration 20 is practically non-existent. As a result, the overall degree of collapse of the microbubbled web 4 shown in FIG. 10 much more closely resembles that of the prior art microapertured web 210 shown in FIG. 9 than that of the prior art embossed web 110 shown in FIG. 6.

It will be observed, however, when comparing the prior art microapertured web 210 of FIG. 9 with the microbubbled web 4 of FIG. 10 that the total area of contact between the microapertured surface aberrations 220 is much less than for the microbubbled surface aberrations 20. Because of the larger contact area and the relatively pliable nature of the thin membranes comprising microbubbles 40, lateral stroking movements by the papillary ridges 16 of the skin 15 on the observer's finger generally experience a higher level of surface friction than is experienced on the prior art microapertured web 210 generally shown in FIG. 9. As a result, although microbubbled webs of the present invention exhibit approximately the same degree of softness, i.e., resistance to collapse, as comparably patterned prior art microapertured webs of the type shown in FIG. 9, they are generally perceived as more suede-like than prior art microapertured webs of the type shown in FIG. 9.

Figure 11:
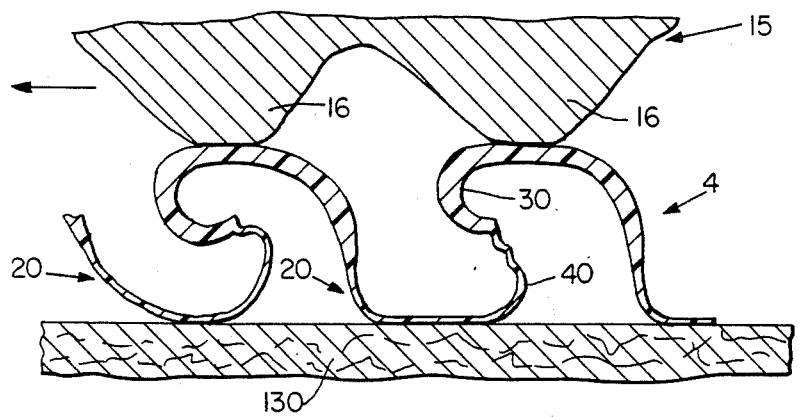
FIG. 11 is a simplified cross-sectional illustration of a "planar" web of the type shown in FIGS. 3 and 10, but illustrating a somewhat different behavior when the microbubbles of the surface aberrations are oriented toward rather than away from the absorbent element of the disposable absorbent structure.

While suede-like tactile impressions are generally regarded as favorable by most consumers, there may be situations wherein it is desirable that the exposed surface of the web not be capable of exhibiting a high degree of surface friction. FIG. 11 is a cross-sectional illustration generally similar to that of FIG. 10, but showing the interaction between the web 4 and the papillary ridges 16 of the skin 15 on the user's finger when the web is oriented so that the microbubbled portions 40 of the surface aberrations 20 are oriented so that they do not contact the user's skin in use.

In the web embodiment illustrated in FIG. 11, the microbubbled portions 40 are oriented so that they contact the absorbent substrate 130 rather than the papillary ridges 16 of the user's skin 15. Although the web 4 illustrates almost the same degree of vertical compression in response to the application of comparable vertical forces, the frictional resistance to movement of the user's finger across the surface of the web is much less pronounced. This is believed due to the fact that the relatively pliable membrane portions of the microbubbles 40 do not actually come into contact with the papillary ridges 16 of the user's finger. Although the microbubbles 40 tend to permit overall collapse of the web in a vertical direction, orienting the microbubbles toward the absorbent substrate 130 exposes the thicker lowermost surface of the web to the user's skin. Due to its greater thickness, the portion of the web contacting the wearer's skin is less prone to conform and cling to the wearer's skin, thereby minimizing the area of contact with the skin. Accordingly, orienting the microbubbled surface of webs of the present invention away from the user's skin, as shown in FIG. 11, reduces the surface friction of the web.

Although microbubbled webs of the present invention, when installed in the orientation shown in FIG. 11, may not produce as strong a cloth-like visual and tactile impression, this orientation of the web may be preferred in situations where "noise" reduction is important, but high surface friction is undesirable. Interestingly, the visual acuity of the pattern comprising the bottoms of the surface aberrations 20 is generally perceived as "sharper" than for the microbubbled surface of the web due to the fact that the surface aberrations 20 cannot in any way obscure the pattern of debossments present on the female surface of the web.

Regardless of which direction the microbubbles are oriented in use, substantially fluid-impervious microbubbled polymeric webs of the present invention, such as "planar" web 4 shown in FIGS. 10 and 11, are surprisingly "quiet" when subjected to movement. This is particularly true in situations where they are used as a substantially fluid-impervious backsheet on a disposable absorbent bandage such as the disposable diaper 1 shown in FIGS. 1 and 2. Specifically, substantially fluid-impervious microbubbled polymeric webs of the present invention are much less prone to make "rattling" or "rustling" noises than otherwise identical fluid-impervious embossed structures having similar patterns of fine scale surface aberrations which do not include microbubbles coincident with their points of maximum amplitude. The dramatic reduction in "noise" had previously been obtainable only by microaperturing the polymeric film generally in accordance with the teachings of the aforementioned commonly assigned U.S. Pat. No. 4,629,643 to Curro et al., thereby rendering it fluid permeable.

While not wishing to be bound, it is believed that the flexible membranes comprising the microbubbles 40 located at the end of each of the surface aberrations 20 in substantially fluid-impervious webs of the present invention provide flex points or hinges in the web 4, in a manner similar to the microapertures in webs of the type disclosed in the aforementioned commonly assigned U.S. Patent to Curro et al. As a direct consequence, substantially fluid-impervious microbubbled webs of the present invention are less stiff than prior art fluid-impervious webs exhibiting a similar pattern of non-microbubbled surface aberrations. Polymeric webs which are less stiff generally produce less "noise" when subjected to motion than stiff webs. Additionally, the highly thinned and flexible membranes comprising the microbubbles 40 are not able to effectively couple mechanical motions induced in the web to the surrounding air. As a result, sound generation, which largely depends upon the degree of coupling, is significantly reduced compared to prior art polymeric webs not exhibiting the highly thinned, flexible microbubbled surface aberrations.

Figure 3A:
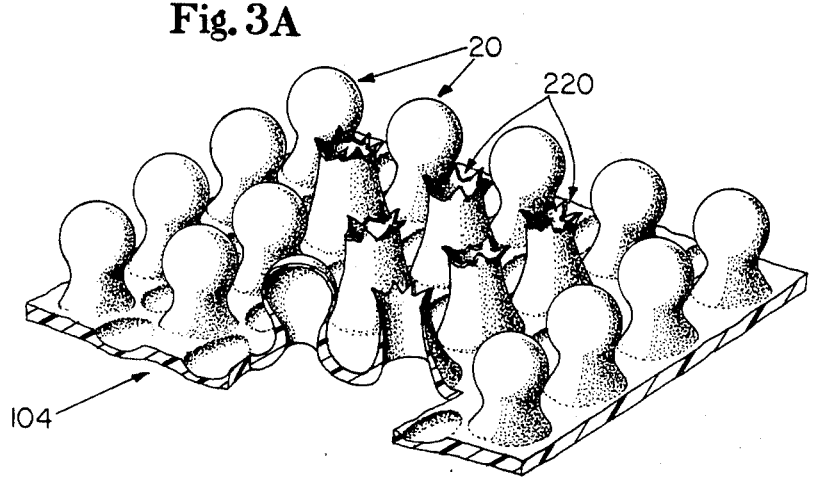
FIG. 3A is an enlarged perspective illustration of a hybrid microbubbled/microapertured web structure exhibiting both microbubbled and microapertured surface aberrations in a predetermined pattern along its surface.

"Quiet", cloth-like, microbubbled plastic webs of the present invention may be made in several different ways. In addition the webs may be made in "planar", or "macroscopically expanded" configurations. If fluid impermeability is not a requirement, the microbubbled webs can also be microapertured in predetermined locations to provide a substantially uniform tactile impression and appearance, but fluid permeabilty only in predetermined portions of the web. FIG. 3A is representative of such a hybrid web structure 104 wherein the microbubbled surface aberrations are designated 20 and the microapertured surface aberrations are designated 220. In addition, microbubbled webs of the present invention can also be "macroscopically expanded and macroscopically apertured".

THE MUSHROOM-LIKE CROSS-SECTIONAL APPEARANCE OR SHAPE OF SURFACE ABERRATIONS OF THE PRESENT INVENTION

As has been pointed out earlier in the present specification, microbubbled surface aberrations in webs of the present invention exhibit a mushroom-like cross-sectional appearance or shape when viewed from a side elevation. This is due to the fact that the minimum internal cross-sectional area of the thicker base portion, as measured approximately where the base portion is joined to the microbubbled portion of the surface aberration in a plane-oriented perpendicular to the amplitude of the surface aberration, is normally smaller than the maximum internal cross-sectional area of the microbubbled portion, as measured in a parallel plane. Because of the extremely thin membrane-like behavior of the microbubbled portion of the surface aberration, it may be necessary to subject the web samples to be evaluated to a slight fluid pressure to fully expand the microbubbled portion of the surface aberrations prior to determining if the aforementioned cross-sectional area relationship is present in any given web sample. A relatively low pneumatic pressure applied to the female surface of the web will in most instances suffice.

A particularly preferred method for analyzing the cross-section of the surface aberrations involves casting samples of the film while it is in its fully expanded condition, and thereafter photographing, on a highly enlarged scale, very thin cross-sectional slices taken from the casting. This procedure is described in detail in the following paragraphs. It must, of course, be recognized that it will in some instances be possible to produce sliced web samples of the present invention wherein the microbubbled portion of a given surface aberration may not exhibit a mushroom shaped cross-section when viewed from a particular side elevation. This may in fact be due to where the section is taken through the particular surface aberration rather than a failure of the surface aberration to satisfy the cross-sectional area relationship described earlier herein, i.e., the same surface aberration, if sectioned along a different axis, may indeed exhibit a mushroom-like cross-section. Therefore, an analysis undertaken to determine if a mushroom-like cross-section exists in the vast majority of surface aberrations present in any given web sample should simultaneously examine a multiplicity of surface aberrations rather than an isolated surface aberration.

METHOD FOR PREPARING AND PHOTOGRAPHING FILM SAMPLES TO CHECK FOR MUSHROOM-LIKE CROSS-SECTIONAL SHAPE OR SURFACE ABERRATIONS

This method involves three steps, embedding, microtoming, and the photography of the film samples in question.

I. Procedure for Embedding Film Samples

The procedure for embedding film samples to be microtomed is as follows:

1. Cut film into samples measuring approximately 2⅛ inches × 1¼ inches and put into cardboard frame having an opening measuring approximately 1¾ inches × 1 inch. Use a stapler to staple the frame to the film.

2. Using a metal vapor deposition apparatus such as a Balzer's Model No. 5CD030 available from Balzer's Union Corporation of Hudson, N.H., gold coat a thin metal coating onto each side of the film sample following manufacturers instructions. The gold coating promotes the wetting and adhesion of the embedding liquid.

3. The following components are mixed and used as an embedding solution: 60 mls. Versamid 125 as available from Henkel Corporation of Minneapolis, Minn.; 40 mls. of either Epon 812 or Pelco Medcast, as available from Ted Pella, Inc. of Tustin, Calif.; and 30 mls. 1,1,1-trichloroethane in a beaker (stir until well mixed).

4. Pour embedding solution into a silicone rubber mold having a cavity shaped to accommodate the cardboard frame and a depth of approximately ¼ inch until it has a depth of about 5 millimeters.

5. Slide the gold-coated film sample (having the microbubbled portion of the surface aberrations downwardly oriented) just under the surface of the embedding solution. Special attention must be taken to insure that no air bubbles have become trapped under the surface of the film.

6. Continue to pour more embedding solution into the silicone rubber mold until it is full to ensure that the film sample is completely submerged.

7. Place the mold in a vacuum desiccator such as a Sleeve Top Desiccator, CMS Model No. 076-745 available from Curtis Matheson Scientific of Cincinnati, Ohio. Apply a level of vacuum which is sufficient to remove air bubbles from the embedding solution, but insufficient to raise the film sample to the surface of the embedding solution. When all of the bubbles in the solution have risen to the top, turn the vacuum off and let the sample sit 24 hours. The embedding solution should be hard. If so, the sample is ready to be removed from the mold. If the sample is easily deformable to the touch, then the sample can be removed from the desiccator and set at room temperature until it is hard.

8. Remove the sample from the mold. Using a cutting knife, cut the cardboard frame from all four edges. The sample should now be rectangular in shape, measuring approximately 1½ inches × 1 inches.

II. Microtoming/Microscope Slide Preparation

1. Place the prepared embedded film sample block into the microtome lengthwise, trying to get it as level as possible. Make several cuts until a smooth surface is generated. Once the surface is smooth, start making as thin slices as possible. Ten micron slices should be achievable. Carefully remove the slices from the microtome blade to a microscope slide, being sure not to lap or twist the slices.

2. Three to four slices can be mounted on a microscope slide using oil and a coverslip.

3. At this point, use an optical microscope to check the slices to be sure that none of them have become overlapped, etc.

III. Photographing Film Sample

1. Place the prepared microscope slide under a trinocular microscope such as an American Optical Model Series 10 Microstar, as available from Americal Optical Corporation of Buffalo, N.Y., with a camera such as a Nikon Model FT, as available from Nikon Inc. of Garden City, N.Y., mounted on it. Set the magnification to get the number of surface aberrations desired into the field of view (40X to 100X). Looking through the camera, focus. Since the cross-section will likely be thicker than the depth of field or differ in elevation by more than the depth of field only one optical section will be in focus at one time. It will be necessary to continually change the focus, bringing into sharpness successive levels of the specimen until the area of interest is clear. It should also be noted that there exists an unavoidable trade off between depth of field and resolving power. Once the area of interest is in clear focus, you are ready to take the photo. Black and white film is better for high contrast pictures.

2. Set the camera speed, aperture, etc. to the proper mode for the film that you are using. Set the light source on the microscope to the proper setting to give a good reading on the camera's light meter, and take the photo.

WHAT IS MEANT BY SUBSTANTIALLY FLUID-IMPERVIOUS

As will be appreciated by those skilled in the art, microbubbled webs of the present invention will in most instances exhibit some degree of rupturing of the microbubbles of the surface aberrations without destroying the web's substantially fluid-impervious nature. Accordingly, when the term "substantially fluid-impervious" is utilized in describing webs of the present invention, this should not be taken to mean 100 percent fluid-impervious. Furthermore, using the test procedures described in the following paragraphs, it must be recognized that even microapertured webs of the type described in the aforementioned commonly assigned U.S. Pat. No. 4,629,643 to Curro et al. will exhibit a degree of resistance to fluid transmission due to the surface tension effects of the test liquid on the relatively small apertures present in the surface aberrations. Thus, when a microbubbled web of the present invention is characterized as "substantially fluid-impervious", as that term is utilized herein, it shall be taken to mean that the microbubbled portion of the web being subjected to evaluation shall be capable of supporting a hydrostatic head of at least about four (4) inches of liquid water at a temperature of approximately 70° F., as measured in accordance with the test procedures described herein.

METHOD FOR DETERMINING IF FILM SAMPLES ARE SUBSTANTIALLY FLUID-IMPERVIOUS

Test Apparatus

Figure 22:
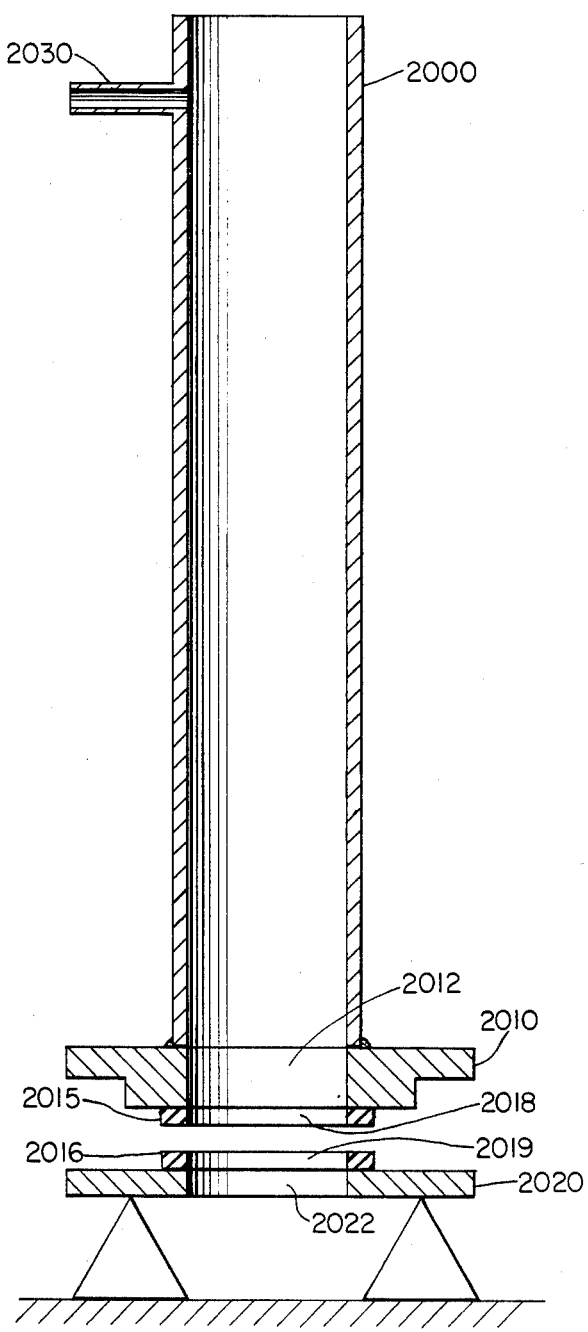
FIG. 22 is a simplified schematic representation of an apparatus for testing web samples for substantial fluid-imperviousness to liquid water.

For a description of the test apparatus described below, refer to FIG. 22.

1. Transparent plexiglass column or tube (2000), 25 inches long and 1 inch inside diameter. Attached to the base of the column is a flange (2010) 4 inches in diameter and a rubber gasket (2015) both with 1 inch diameter holes (2012,2018 respectively) centered with the opening in the column.
2. Plexiglass plate (2020), 4 inches×4 inches×¼ inch thick with a 1 inch diameter hole (2022) in the center and a rubber gasket (2016) with a matching 1 inch diameter hole (2019). Locator pins (not shown) extending down from the flange fit into holes drilled in the plate so that plate and column can be aligned easily and accurately.
3. Tygon tubing connects a distilled water source to the inlet (2030) to the column at a point 24 inches above the base of the column.
4. The assembly is positioned on a pair of supports, as schematically shown in FIG. 22, so that any water passing through the hole (2022) in the base plate (2020) can be readily observed.

Procedure

1. Cut a 2¼ inch×2¼ inch sample of the film to be tested.
2. Place the sample over the rubber gasket (2016) of the plate (2020) such that the microbubbled portion of the surface aberrations of the film sample are downwardly oriented.
3. Using the locator pins (not shown) position the plate under the base of the column (2000).
4. With either spring clamps or 'C' clamps clamp the plate (2020) to the column flange (2010).
5. Add distilled water at a temperature of approximately 70° F. to the column through the inlet (2030). The rate at which water is added should be continuous and slow enough that it trickles down the sides of the column (2000) and does not free fall to the film sample.
6. As soon as the first drop of water falls through the film sample located at the base of the column (2000) record the height of the water in the column. The first drop of water falling through the hole (2022) in the base plate (2020) indicates that water has passed through the film.
7. For any given type of film to be evaulated, 10 repetitions of this test should be done and the reported values averaged.

PREFERRED STARTING MATERIALS

In general, it has been found that preferred starting materials to be used as the incoming film for producing substantially fluid-impervious microbubbled webs of the present invention exhibit a low degree of molecular orientation. The materials also preferably exhibit low-yield and high-elongation characteristics. In addition, the starting films preferably strain harden. Exemplary of preferred starting films are materials such as linear low-density polyethylene, blends of linear low-density polyethylene and low density polyethylene, as available from Ethyl Visqueen of Richmond, Va., linear very-low-density polyethylene as available from Turex, Inc. of Harrisville, R.I.; and block co-polymers such as polyester/polyether which are designated as Hytrel ®, as available from E. I. DuPont de Nemours & Company of Wilmington, Del.

THE HIGH PRESSURE LIQUID STREAM PROCESS EMBODIMENT OF FIG. 12

Figure 12:
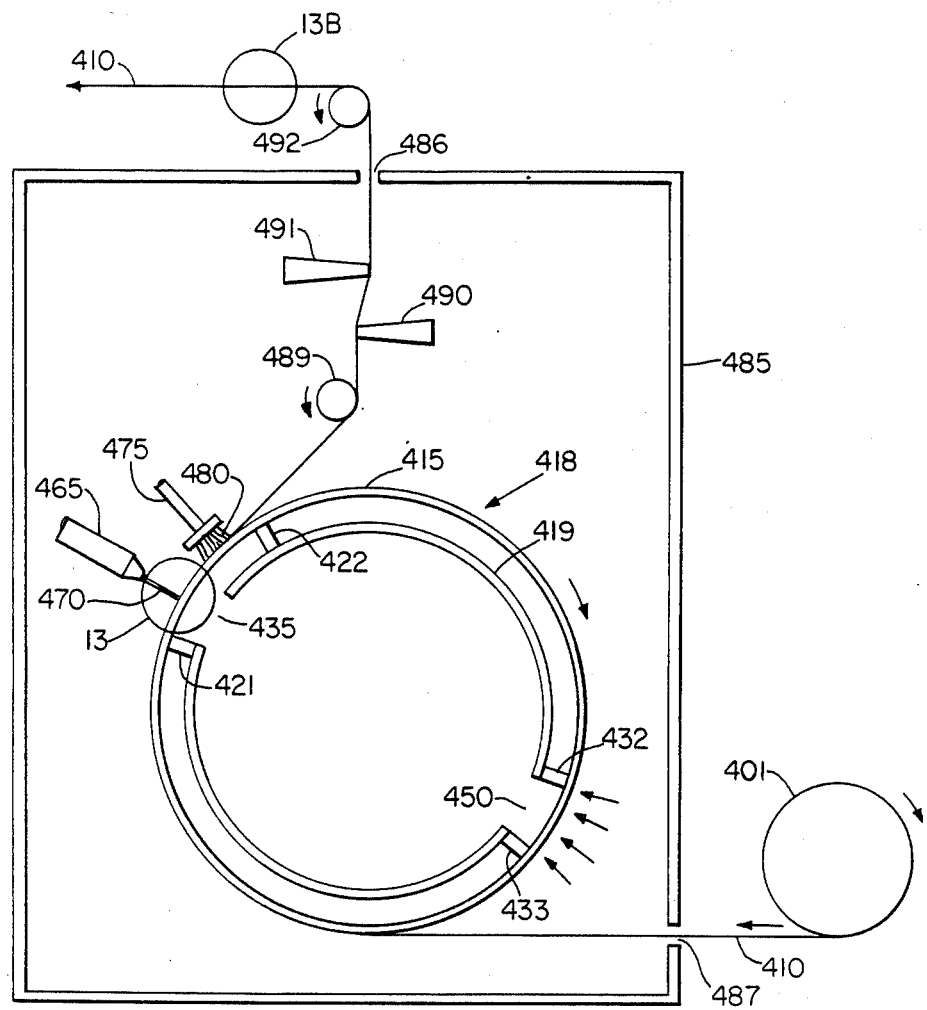
FIG. 12 is a simplified cross-sectional schematic illustration of a continuous process for producing "planar" substantially fluid-impervious microbubbled webs of the present invention.

FIG. 12 is a simplified cross-sectional schematic illustration depicting a particularly preferred method for producing "planar", substantially fluid-impervious, microbubbled webs of the present invention. In the process embodiment shown in FIG. 12, a web of substantially planar film 410 comprised of a polymeric material such as polyethylene is fed from a supply roll 401 onto the surface of a forming drum 418 about which a forming structure 415 continuously rotates at substantially the same speed as the incoming web. The forming drum 418 preferably includes an internally located vacuum chamber 419 which is preferably stationary relative to the moving forming structure 415. A pair of stationary vacuum seals 421,422 approximately coinciding with the beginning and end, respectively, of the vacuum chamber's first inlet 435 are used to establish a seal between the innermost surface of the rotating forming structure 415 and the first vacuum chamber inlet 435. An additional pair of seals 432,433 establish a similar seal between the innermost surface of the rotating forming structure 415 and a second vacuum chamber inlet 450. The second vacuum chamber inlet 450 is positioned in an area of the forming drum 418 where it will not be blocked by the web of film 410.

Opposite the first vacuum chamber inlet 435 there is preferably provided means for applying a fluid pressure differential to the substantially planar web of polymeric film 410 as it traverses the area of the forming drum intermediate vacuum seals 421,422. In the illustrated embodiment, the fluid pressure differential applicator means comprises a high pressure liquid nozzle 465 which discharges a jet of high pressure liquid 470, such as water, substantially uniformly across the entire width of the moving polymeric web 410. The water is preferably applied at a pressure of at least about 350 N/cm² (500 psig), most preferably at least about 700 N/cm² (1,000 psig). The water is also preferably applied at an elevated temperature which is below the transformation temperature range of the incoming polymeric web so that the web remains in a substantially solid state throughout the entire process. This preserves the physical properties and thermo-mechanical history of the incoming web. Details as to the effects of varying the water temperature and the preferred construction and positioning for high pressure liquid nozzle 465 are set forth in commonly assigned, allowed U.S. Patent Application of John Joseph Curro, Alan James Trusty and George Merrill Vernon, Ser. No. 580,911, filed on Feb. 16, 1984 and issued on Sept. 22, 1987 as U.S. Pat. Nos. 4,695,422, and also in 4,609,518 issued to Curro et al. on Sept. 2, 1986, said commonly assigned U.S. Patent Application and said commonly assigned U.S. Patent being hereby incorporated herein by reference.

However, the processing system schematically illustrated in FIG. 12 differs from those described in aforementioned commonly assigned, allowed U.S. Patent Application in the names of Curro et al. and the aforementioned commonly assigned U.S. Patent to Curro et al. in that the web of polymeric film 410 employed in practicing the present invention remains substantially unapertured throughout the entire process. When a polymeric web is apertured in the pattern of a forming structure using a high pressure liquid jet, as generally disclosed in the aforementioned allowed U.S. Patent Application in the names of Curro et al. and in the aforementioned commonly assigned U.S. Patent to Curro et al., the vacuum existing within the forming drum normally causes a high volume of air to flow through the web immediately upon aperturing of the film. This results in (1) adiabatic cooling of the formed and apertured material, (2) adiabatic cooling of the forming structure and (3) venting/cooling of the forming cabinet housing the entire process.

When it is desired to create a microbubbled web of the present invention, or for that matter any formed but unapertured web, this high flow of air which normally occurs as soon as the web is apertured is not established. As a result, the formed but substantially unapertured polymeric web remains at a higher temperature, as does the forming structure and the interior of the forming cabinet. In some instances, the higher temperature imparts to the web a sufficiently low modulus that it will not resist edge curling or the effects of tension induced strain, thereby causing severe instability and roping of the web as it is withdrawn from the surface of the forming structure.

In order to avoid these problems on substantially unapertured webs, the following changes were made to the process generally disclosed in the aforementioned commonly assigned, allowed U.S. Patent Application in the names of Curro et al.:

(1) A continuous film of cooling water 480 is applied to the exposed surface of the web 410 via a low pressure liquid nozzle 475, as generally shown in FIG. 12. The water is preferably flooded onto the film prior to its removal from the forming structure 415, but subsequent to its formation by the high pressure liquid jet 470.

(2) An additional vacuum chamber inlet 450 is provided in the centrally located vacuum manifold 419. This second vacuum chamber inlet 450 is provided in an area of the forming drum 418 where the forming structure 415 is unobstructed by the web of film 410. In the embodiment disclosed in FIG. 12, the second vacuum inlet 450 is positioned at approximately four o'clock. The second vacuum inlet 450 reestablishes vacuum induced air flow through the rotating forming structure 415 to cool the forming structure and to provide internal venting/cooling of the cabinet 485 enclosing the forming drum 418 and the high pressure liquid nozzle 465.

(3) Finally, the web path is redirected inside the cabinet 485, as generally shown in FIG. 12, to provide the shortest possible traverse through the cabinet. In particular, the unprocessed flat polymeric web 410 enters the cabinet through inlet slot 487, is carried by the rotating forming structure 415 about approximately half the periphery of the stationary forming drum 418 and is thereafter removed via idler rolls 489 and 492 for final drying and either rewinding or end use applications. A pair of opposed rubber blades 490,491 provide bulk dewatering of the web by producing a squeegee-like action on the microbubbled web 410 as the web passes between idler rolls 489 and 492. Routing the web in the manner shown in FIG. 12 minimizes any reheating of the web after it has been cooled by the film of cooling water 480 applied by low pressure liquid nozzle 475.

Figure 13:
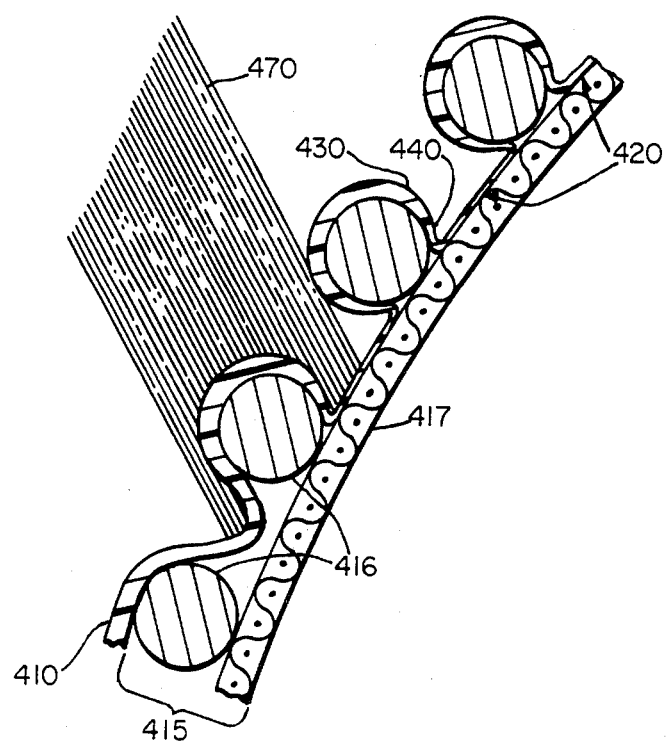
FIG. 13 is a greatly enlarged cross-sectional view illustrating the manner in which the high pressure liquid jet creates surface aberrations having a microbubble at their point of maximum amplitude in webs of initially flat polymeric film, said cross-section being taken at point corresponding to inset 13 in FIG. 12.

FIG. 13 is a greatly enlarged view of inset 13 shown in FIG. 12. In the preferred illustrated embodiment, the forming structure 415 utilized to produce "planar" microbubbled plastic webs of the present invention is constructed of a pair of woven wire layers which are preferably laminated together by a process which does not destroy the porosity of either layer. The outermost layer, which is much coarser than the innermost layer, is preferably comprised of woven wire filaments 416 having a diameter of about 9 mils (0.009 inches) or less and a mesh count of at least about 50 filaments per lineal inch by about 50 filaments per lineal inch, most preferably about 80 filaments per lineal inch by about 80 filaments per lineal inch. The overall thickness of the outermost layer of woven wire is typically between one (1) and two (2) times the maximum dimension of the interstitial openings formed between intersecting filaments 416 of the woven wire layer, as measured about the periphery of forming structure 415.

To permit reliably forming the relatively thick base portions 430 and thinning of the tips of the surface aberrations 420 of the web 410 without also permitting rupture of the thinned portions, a second porous layer shown schematically as 417 in FIG. 13 is preferably provided immediately adjacent the innermost surface of the outermost woven wire layer. As mentioned earlier herein, placing the second porous layer at the optimum depth below the surface of the outermost layer will permit thinning of the surface aberrations to form microbubbles at their tips, yet will provide sufficient support to the thinned microbubbles, to substantially prevent their rupture.

Determination of the optimum depth of placement of the innermost layer below the surface of the outermost layer is best done empirically on a case-by-case basis for any given web material, thickness and pattern of surface aberrations. In general, reducing the depth of placement of the second finer mesh porous support member will reduce the amount of rupturing of the microbubbles. Conversely, increasing this depth will increase the amount of rupturing of the microbubbles.

Since the second or innermost layer is normally placed immediately adjacent the innermost surface of the first or outermost layer, the depth of placement of the second support member is normally determined by the thickness of the first support member. Accordingly, the way to vary the depth of placement of the second support member is to vary the thickness of the first support member. For woven wire support members this thickness can be varied either by calendering the first woven wire support member or by varying the diameter of the wires with which it is woven. When the first support member is a laminate forming structure comprised of thin, apertured sheets of the type generally disclosed in commonly assigned U.S. Pat. No. 4,342,314 issued to Radel et al. on Aug. 3, 1982, which is hereby incorporated herein by reference, the thickness of the forming structure can be varied as desired by adding or deleting thin apertured sheets when constructing the laminate forming structure.

In order to provide support to the highly thinned membranes comprising the microbubbles, the second or innermost layer 417 exhibits a much finer degree of porosity than the outermost layer. The second porous layer 417 may also, if desired, be comprised of woven wire. In a particularly preferred embodiment, porous layer 417 is comprised of filaments having a diameter of about 3 mils (0.003 inches) or less and a mesh count between about 165 filaments per lineal inch by about 800 filaments per lineal inch and about 325 filaments per lineal inch by about 2,300 filaments per lineal inch in a twilled Dutch weave pattern (there is a degree of filament overlap with this pattern).

When placed at the proper depth, as described above, it has been learned that if the interstitial openings formed between the intersecting filaments in porous layer 417 are between about 0.5 mils and about 1.0 mils, then the underlying porous layer 417 will allow venting of any air trapped between plastic web 410 and the outermost woven wire layer comprised of intersecting filaments 416, yet will provide enough support to the web 410 to substantially prevent rupturing of the thinned portions of the web ultimately comprising microbubbles 440. In this regard it should be noted that any bonding process which is used to laminate the outermost and innermost layers to one another must avoid the creation of a liquid state in any of the materials contained in either layer or the porosity of the innermost layer is likely to be impaired, i.e., the capillary attraction of the tiny pores tends to cause filling of the pores by the liquid, thereby decreasing the porosity of the innermost layer. Accordingly, substantially dry bonding processes, such as diffusion bonding as performed by the Facet Company of Greensboro, N.C., are particularly preferred when constructing laminate forming structures used in practicing the present invention.

If used without an underlying porous layer 417, the outermost woven wire layer comprised of filaments 416 shown in FIG. 13 could be utilized to produce either microapertured webs of the type disclosed in the aforementioned commonly assigned U.S. Pat. No. 4,629,643 to Curro et al. or microbubbled webs of the type disclosed herein. In the event no support is provided to the plastic web 410 at the interstitial openings formed in the woven wire outermost layer, then the force and mass flux of the high pressure liquid jet must be carefully regulated to a predetermined maximum which is insufficient to cause rupturing of the film. Otherwise, the unsupported tips of the surface aberrations formed in the web by the high pressure liquid jet will be thinned and ruptured to form microapertures of the type disclosed in the aforementioned commonly assigned U.S. Pat. No. 4,629,643 to Curro et al.

Because it has generally been found more difficult to precisely control the force and mass flux of the high pressure liquid jet to ensure the formation of microbubbled surface aberrations without also causing rupturing, it is generally prefered to use the secondary porous layer 417, in all areas of the web to be microbubbled. The secondary porous layer 417 is most preferably eliminated only in those areas where microaperturing of the surface aberrations is desired.

As will be appreciated by those skilled in the art, the laminate forming structure 415 schematically illustrated in greatly enlarged form in FIG. 13 is relatively delicate. It is therefore generally preferable to provide some additional mechanical support (not shown in FIG. 13) for the forming structure against the innermost surface of the porous layer 417. One technique for providing such mechanical support to the relatively delicate forming structure is disclosed in commonly assigned U.S. Pat. No. 4,151,240 issued to Lucas et al. on Apr. 24, 1979, which U.S. Patent is thereby incorporated herein by reference. Another technique is to provide a rotating honey-comb patterned support roll underlying porous layer 417. Still another possible technique is to employ an apertured stationary support member in the area of vacuum chamber inlet 435, as generally disclosed in the commonly assigned British Patent Application of William I. Mullane, Publication No. 0138601, available to the public on Apr. 24, 1985 and hereby incorporated herein by reference. The exact nature of the mechanical support employed is not critical to the practice of the present invention. What is important is that each of the interstitial openings formed in the outermost woven wire layer by intersecting filaments 416 be allowed to vent through at least a portion of the underlying porous layer 417 as the web 410 undergoes deformation due to the influence of the high pressure liquid jet 470.

Once the web 410 shown in FIG. 13 leaves the influence of high pressure liquid jet 470, its temperature is lowered by a film of cooling water 480 applied by low pressure liquid nozzle 475. It is thereafter removed from the rotating forming structure 415, passed about a first idler roll 489, between a pair of opposing rubber squeegee blades 490,491 to remove the bulk of the water therefrom, and finally about a second idler roll 492. From this point the "planar" microbubbled web 410 is preferably subjected to further drying to remove any remaining water therefrom, after which it is either rewound onto rolls for use at a later time or forwarded directly to end use applications.

Figure 13A:
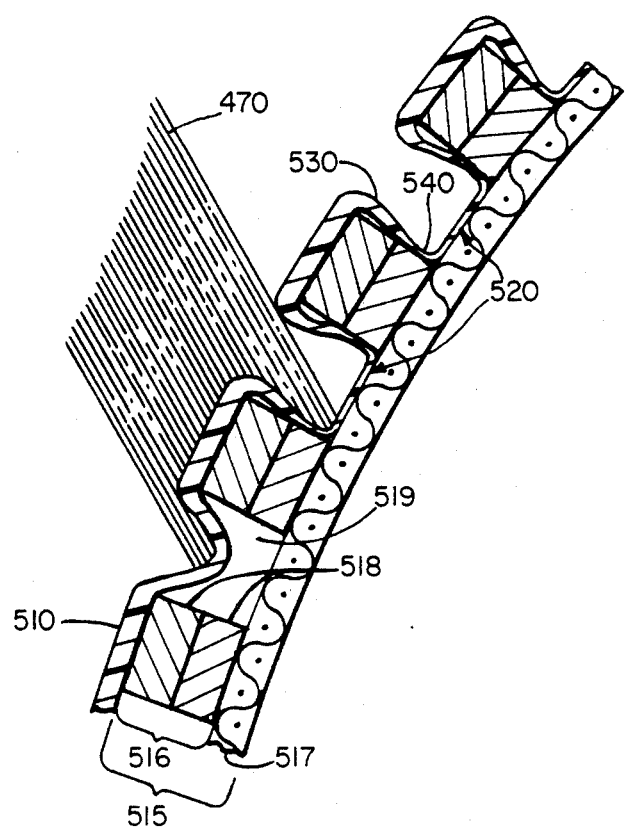
FIG. 13A is a greatly enlarged cross-sectional illustration generally similar to that of FIG. 13, but illustrating the use of a different type of forming structure.
Figure 13B:
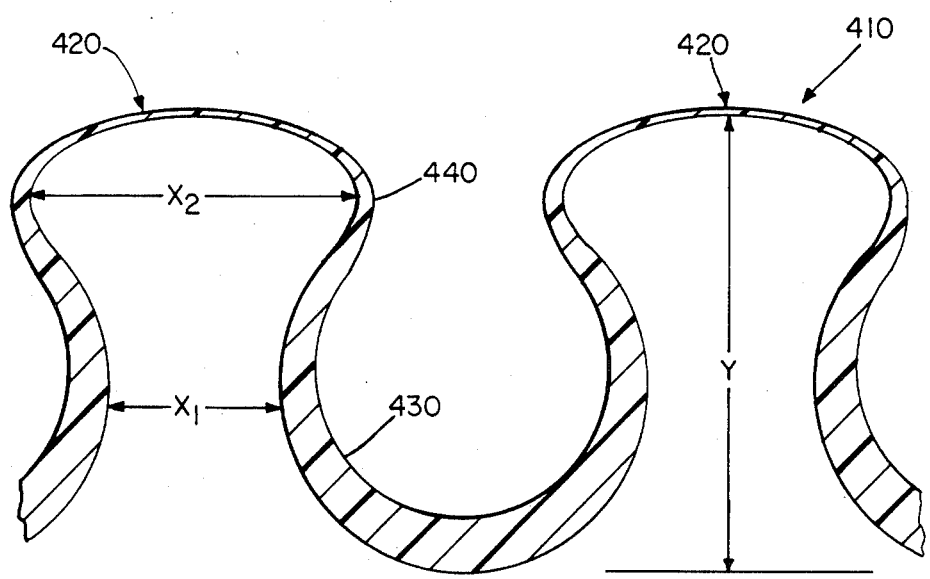
FIG. 13B is a greatly enlarged cross-sectional view of a "planar" microbubbled web of the present invention produced via the process of FIGS. 12 and 13, said cross-section being taken at a point corresponding to inset 13B in FIG. 12.

The resultant microbubbled web 410 is shown in greatly enlarged form in FIG. 13B, which was taken at a point corresponding to inset 13B in FIG. 12. The upwardly oriented thinned microbubbled portions 440 of the surface aberrations 420 are substantially the same as thinned microbubbled portions 40 of the surface aberrations 20 of web 10, shown in FIGS. 3 and 4. The relatively thicker base portions 430 of web 410 are substantially the same as relatively thicker base portions 30 of web 10, shown in FIGS. 3 and 4. As can also be observed from FIG. 13B, each microbubbled surface aberration 420 exhibits a mushroom-like cross-section when viewed from a side elevation. The minimum internal cross-sectional area of the relatively thicker base portion 430, as measured in a plane approximately coinciding with where the base portion 430 is joined to the microbubbled portion 440 of the surface aberration (e.g., plane $X_1$ in FIG. 13B), is typically smaller than the maximum internal cross-sectional area of the fully expanded microbubbled portion 440, as measured in a parallel plane (e.g., plane $X_2$ in FIG. 13B) oriented perpendicular to the amplitude or axis Y of the surface aberration.

FIG. 13A is a greatly enlarged cross-sectional view generally similar to that of FIG. 13, but employing an alternative forming structure 515 to produce a microbubbled web 510 of the present invention. The innermost porous layer 517 generally shown in FIG. 13A may, if desired, be the same as porous layer 417 shown in FIG. 13. However, instead of the woven wire outermost layer illustrated in FIG. 13, the outermost portion 516 of forming structure 515 comprises one or more thin metallic sheets 518, each exhibiting an identical pattern of apertures 519. The thin apertured sheets 518 are preferably made by photoetching techniques, as generally taught by commonly assigned U.S. Pat. No. 4,342,314 issued to Radel et al. on Aug. 3, 1982 and hereby incorporated herein by reference. However, when multiple sheets are employed, the copper plating and furnace brazing technique taught by the aforementioned commonly assigned U.S. Patent to Radel et al. is preferably not utilized to bond them to one another. This is due to the fact that the copper used to bond the sheets 518 to one another can liquefy and impair the porosity of the underlying porous layer 517 when these structures are ultimately bonded to one another. To avoid this problem, the apertured sheets 518 are preferably bonded to one another to form an integral laminate portion 516 using a substantially dry bonding process, such as diffusion bonding as performed by the Facet Company of Greensboro, N.C., and the integral laminate portion 516 is thereafter bonded to the underlying porous layer 517, again using a substantially dry bonding process such as diffusion bonding.

The size and spacing of the apertures 519 formed in the laminate portion 516 of the resultant integral forming structure 515 should correlate reasonably closely to the size and spacing criteria described earlier herein with respect to the woven wire support structure comprised of filaments 416. However, the thickness of the laminate portion of the forming structure should generally be between about one half (½) and about one (1) times the maximum dimension of the apertures 519 in the outermost portion of the forming structure.

As can be seen in FIG. 13A, the high pressure liquid jet 470 causes the flat incoming polymeric web 510, which can be identical to incoming web 410 shown in FIGS. 12 and 13, to substantially conform to the image of the forming structure 515. As in the case with the outermost woven wire structure shown in FIG. 13, the ends of the surface aberrations 520 formed in web 510 are also substantially thinned to the point that they exhibit a membrane-like behavior. In the case of opaque webs of plastic film, the degree of thinning which occurs in the microbubbled portions 540 of the surface aberrations is usually sufficient that the microbubbled portions of the web appear to be substantially transparent.

Interestingly, although the apertures 519 which comprise the capillary networks in the forming structure 515 exhibit substantially straight-sided walls, microbubbled webs produced using forming structures of the latter type nonetheless exhibit microbubbles having a mushroom-like cross-sectional appearance, i.e., the microbubble portion exhibits a greater internal cross-section than the minimum internal cross-section of the base portion of the surface aberration, as measured in parallel planes oriented perpendicular to the axis of the surface aberration. This phenomenon is believed due to the difference in plastic yielding which takes place in the microbubbled portion 540 of the surface aberration compared to the more elastic deformation which takes place in the base portion 530 of the surface aberration. As a result of this difference in plasticity/elasticity, the thicker base portions 530 exhibit a greater degree of recovery once they are removed from the influence of the high pressure liquid jet 470. This greater degree of elastic recovery is illustrated in FIG. 13A, wherein the base portion 530 of the surface aberration 520 which has just passed beyond the influence of the high pressure liquid jet 470, has moved slightly away from the side walls of the aperture 519 which it was produced. Thus, when the microbubbled web 510 is removed from the forming structure 515, the individual surface aberrations 520 will also exhibit a mushroom-like appearance generally similar to, but somewhat less pronounced, than that exhibited by the surface aberrations 420 of microbubbled web 410 shown in FIG. 13B.

EXEMPLARY WEB EMBODIMENT PRODUCED VIA THE PROCESS OF FIG. 12

An exemplary embodiment of a microbubbled web of the present invention was made generally in accordance with the process illustrated in FIG. 12 utilizing a laminate forming structure of the type generally disclosed in Figure 13A.

The starting material comprised a web which was a blend of polyethylenes designated Ethyl Visqueen No. XP-4337, as available from Ethyl Visqueen of Richmond, Va. The initial thickness of the web prior to processing was nominally referred to by Ethyl Visqueen as 1.2 mils (0.0012 in).

The apertured sheet portion of the forming structure was constructed of laminar layers of thin metal, each having circular holes measuring approximately 8 mils (0.008 inches) in diameter. The hole pattern was regularly spaced and exhibited a density of 100 holes per lineal inch by 100 holes per lineal inch. The overall thickness of the apertured laminar sheet portion of the forming structure measured approximately 6 mils (0.006 in). Immediately beneath the laminar apertured sheet portion of the forming structure there was provided a woven wire porous backup layer or screen comprised of filaments having a diameter of approximately 1 mil (0.001 in) arranged in a twilled Dutch weave pattern (there is a degree of filament overlap with this pattern), said screen having a filament density of approximately 325 filaments per lineal inch by approximately 2,300 filaments per lineal inch, as available from the Facet Company of Greensboro, N.C. The laminar apertured sheet portion and the porous backup layer were bonded to one another by diffusion bonding, as performed by the Facet Company, to form an integral forming cylinder which was mechanically supported at its innermost surface without "blinding" the porosity of the innermost screen. The cylindrical forming structure rotated about a stationary drum having a centrally located vacuum chamber, as schematically shown in FIG. 12.

The web was fed onto the aforementioned rotating forming structure at a speed of approximately 300 feet per minute and subjected to a high pressure water jet operating at a gauge pressure of approximately 800 pounds per square inch and a water flow rate of approximately 3 gallons per minute per cross-machine direction inch of web width. The temperature of the water in the high pressure water jet was approximately 180° F., as measured at the nozzles.

Cooling water at a temperature of approximately 50° F. was applied at a rate of approximately 1 gallon per minute per cross-machine direction inch of web width, as schematically shown in FIG. 12.

The vacuum chamber was maintained at approximately 7.5 inches of Mercury to provide screen cooling and chamber venting, as described earlier in the present specification.

The resultant "planar" microbubbled web exhibited a regularly repeating pattern of surface aberrations, each having a highly thinned, mushroom-shaped membrane coincident with its point of maximum amplitude. The density of microbubbled surface aberrations corresponded to the density of the apertures in the laminar apertured sheet portion of the forming structure, i.e., approximately 100 microbubbled surface aberrations per lineal inch by approximately 100 microbubbled surface aberrations per lineal inch. The overall caliper of the resultant "planar" microbubbled web was approximately 6 mils (0.006 in), as measured under a low load condition of approximately 0.21 pounds/in$^2$ (95 grams/in$^2$). The microbubbled portions of the surface aberrations of the opaque web were substantially transparent.

The exemplary web embodiment had a physical appearance generally similar to those illustrated in FIGS. 3, 4 and 13B. When superposed on an absorbent substrate so that the microbubbled portion of the web was outwardly oriented, the web in question exhibited a soft, suede-like tactile impression when stroked laterally by an observer's finger. In addition, the structure was substantially free of "rattling" or "rustling" noises when the microbubbled web and absorbent substrate were subjected to movement beneath the outer garments of a test subject.

THE HYDRAULIC PROCESS EMBODIMENT OF FIG. 14

Figure 14:
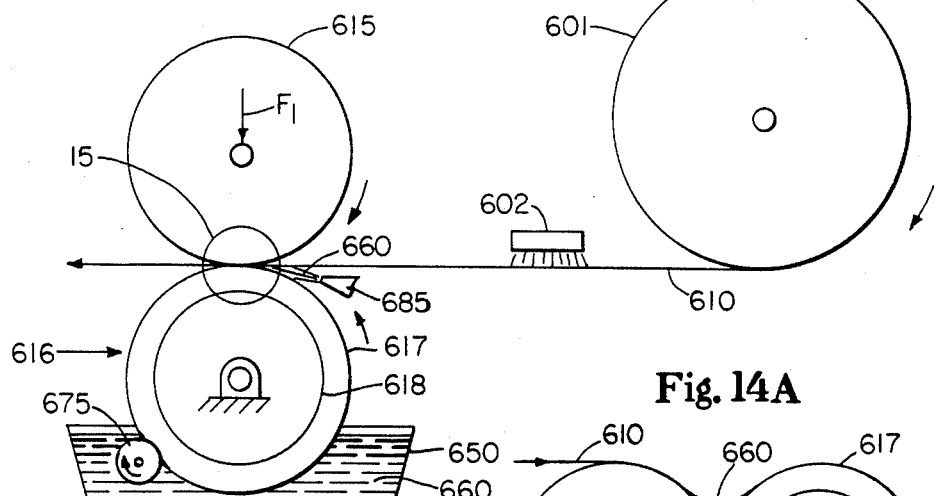
FIG. 14 is a simplified cross-sectional schematic illustration of an alternative hydraulic process for producing "planar" microbubbled webs using hydraulic pressure.

In FIG. 14 there is shown an alternative hydraulic process which can be used to produce "planar" microbubbled webs of the present invention. In the illustrated embodiment, a roll of polymeric film 610, which can be generally similar to polymeric films 410 and 510, is fed from a supply roll 601. If desired, the temperature of the web 610 can be elevated to soften the web and make it more easily deformable by passing it beneath heating means schematically illustrated at 602.

Unlike prior art processes which simply employ mating embossing rolls to deform a heated polymeric web passing therebetween, the embossing rolls illustrated in FIG. 14 employ a liquid such as water 660 to provide hydraulic deformation of the web and thinning of the tips of the surface aberrations so as to form microbubbles therein. In a particularly preferred embodiment, the water 660 in tank 650 is also maintained at an elevated level to soften the web and make it more easily deformable during the embossing process. However, it is preferable that the degree of heating imparted to the web prior to reaching the nip between rolls 615 and 616 not be sufficient to create web sticking problems.

Embossing roll 615 is preferably a hard surfaced roll exhibiting a pattern of female capillary networks corresponding to the pattern of surface aberrations desired in the resultant microbubbled web 610. Lowermost embossing roll 616 preferably comprises a hard surfaced center 618 on which is mounted a rubber or otherwise deformable member having a multiplicity of blind capillary networks 655 about its periphery. As the embossing roll with the deformable member enters the water it is preferably subjected to a contact pressure induced by a submerged, smooth surfaced, hard metal roll 675 rotating in a clockwise direction. The contact pressure generated by the two rolls facilitates the removal of any air that might still remain in the blind capillary networks 655. Water 660 is picked up in the blind capillary networks 655 of the deformable outer layer 617 as embossing roll 616 passes through the liquid filled tank 650.

As the blind capillary networks 655 approach the infeed of the nip formed between the two rolls 615 and 616, more water can be sprayed from a water nozzle 685 onto the surface of the deformable layer 617 of the lowermost embossing roll 616 to ensure flooding of the nip and compensate for any possible water loss which may occur during rotation.

Figure 14A:
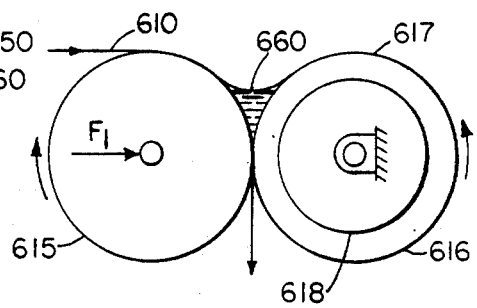
FIG. 14A is a simplified cross-sectional schematic illustration of an alternative embossing roll configuration for a hydraulic pressure process for producing "planar" microbubbled webs.

In an alternate execution of the present invention (not shown), the water tank 650 could be removed altogether and water 660 could be delivered to the nip formed between rolls 615 and 616 through a nozzle or a battery of nozzles 685. The water stream in this alternate execution is aimed substantially at the nip so that water 660 is picked up by the blind capillary networks 655 of the deformable outer layer 617 and carried between rolls 616 and 615 in substantially the same manner illustrated in FIG. 15. In still another embodiment of the present invention shown in FIG. 14A, rolls 615 and 616 could be placed in the same horizontal plane and the nip formed between them flooded with water 660 by gravity to ensure pickup of water by the blind capillary networks 655 on roll 616.

As should be apparent from the foregoing, the particular method utilized to fill the blind capillary networks 655 is not critical.

Figure 15:
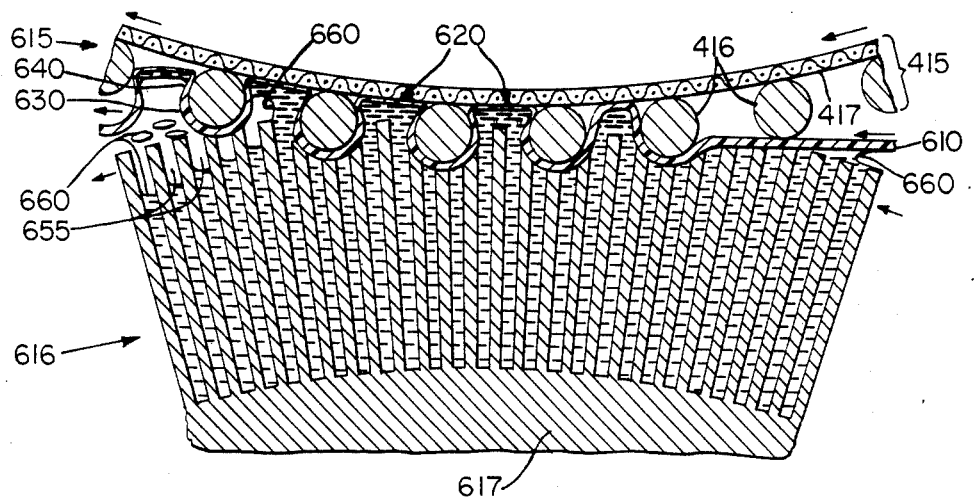
FIG. 15 is a greatly enlarged cross-sectional view of the pressure nip segment which is employed in the hydraulic embossing roll system shown in FIG. 14, said view being taken at a point corresponding to inset 15 in FIG. 14.

The nature of the embossing and thinning operation is schematically shown in greater detail in the greatly enlarged cross-section of FIG. 15, which is taken at inset 15 in FIG. 14. The outermost surface of embossing roll 615 can, if desired, be substantially the same as forming structure 415 illustrated in FIG. 13. However, unlike the process embodiment disclosed in FIGS. 12 and 13, the volume of liquid applied to the lowermost surface of web 610 by embossing roll 616 is largely controlled by the size and spacing of the blind capillary networks 655 on the surface of embossing roll 616. Therefore, it is not an absolute requirement that the forming structure 415 employ a finer mesh innermost porous layer 417, such as is illustrated in FIG. 15. If a finer mesh innermost porous layer 417 is not employed or if the innermost porous layer 417 is located too far below outermost layer 416 to provide support to the microbubbles 640 formed in the surface aberrations 620 in the web 610, then the blind capillary networks 655 in deformable roll 616 must be sized and spaced so that the volume of liquid acting upon the web opposite any particular opening in the forming structure 415 will be just sufficient to plastically deform the web to create a surface aberration 620 having a microbubble 640 at its tip. If the volume of liquid in the capillary networks 655 is too small, the web will not be sufficiently deformed to create highly thinned microbubbles at the tips of the surface aberrations 620. On the other hand, if the volume of liquid is too large, the microbubbles will be ruptured to produce a substantially microapertured web of the type disclosed in the aforementioned commonly assigned U.S. Pat. No. 4,629,643 issued to Curro et al. on Dec. 16, 1986.

Regardless of whether or not the finer mesh innermost porous layer 17 is employed, there is a need to provide a degree of mechanical reinforcement adjacent the innermost surface of forming structure 415 to prevent deformation thereof in response to the applied force F$_1$ exerted between embossing rolls 615 and 616. Reinforcing techniques of the type generally described in connection with the process embodiment of FIG. 12 can, in most instances, also be employed in the process embodiment of FIG. 14.

FIG. 15 illustrates the nature of the blind capillary networks 655 present in the peripheral surface of deformable layer 617 of embossing roll 616. As can also be seen from FIG. 15, these blind capillary networks 655 are substantially filled with water 660 as they approach the infeed to the nip formed between rolls 615 and 616. As the deformable portion 617 of the lowermost embossing roll 616 begins to undergo deformation, a substantially continuous film of water 660 is created between the lowermost surface of the incoming web of film 610 and the peripheral surface of the deformable portion of the lowermost embossing roll 616. As a result, each of the blind capillary networks 655 in the deformable portion 617 of the lowermost embossing roll is completely filled with liquid by the time it forms a seal against the lowermost surfaces of incoming polymeric web of film 610.

As can be seen in FIG. 15, deformation of the peripheral portion 617 of lowermost embossing roll 616 occurs as the polymeric web 610 advances through the nip formed between rolls 615 and 616. Deformation of the lowermost roll, particularly outermost portion 617 containing the liquid filled blind capillary networks 655, becomes more and more pronounced until it reaches a maximum at a point coinciding with the centerline connecting the axes of rotation of rolls 615 and 616. Because the outermost portion of deformable layer 617 undergoes most of the deformation during the roll's passage through the nip, the incompressible liquid 660 which initially filled all of the uncompressed blind capillary networks 655 experiences a dramatic increase in pressure due to the sharp reduction in volume of the blind capillary networks 655 as they are subjected to extensive compression. Since the outermost surface of deformable portion 617 of the lowermost embossing roll is effectively sealed to the lowermost portion of web 610 at the point of maximum deformation of the capillary networks 655, the incompressible liquid 660 contained in the blind capillary networks attempts to escape and in so doing forces the web 610 to expand into the interstices or capillary networks formed between the intersecting filaments 416 of the outermost woven wire portion of forming structure 415 on the uppermost embossing roll 615.

When the blind capillary network 655 in roll 616 are properly sized and spaced, this hydraulic expansion of the web of film 610 produces an end result generally similar to the high pressure liquid jet process embodiment illustrated in FIG. 12. In particular, surface aberrations 620 generally corresponding to the interstices in the woven wire outermost layer on embossing roll 615 are formed in the resultant web. Maximum hydraulic expansion of the web 610, which occurs as the deformable liquid laden lowermost roll 616 undergoes maximum deformation, also causes the tips of each of the surface aberrations to undergo plastic deformation, thereby forming a thin, pliable, continuous membrane, i.e., a microbubble, 640 at the tip of each surface aberration 620, while the base portion 630 of the surface aberration remains relatively thicker.

Once the plastic web 610 passes through the midpoint connecting the axes of rotation of rolls 615 and 616, the hydraulic pressure acting upon the lowermost surface of the film is gradually relieved until such time as the seal between the exterior portion of roll 616 and the lowermost surface of microbubbled web 610 is essentially broken. At this point, a small amount of liquid remains inside the microbubbled portions 640 of the surface aberrations 620 formed in web 610 and a portion of the liquid also remains in the blind capillary networks 655, as generally shown in FIG. 15. Accordingly, the microbubbled "planar" web 610 is preferably subjected to further drying and thereafter rewound or fed directly to end product applications. Meanwhile, the partially filled blind capillary networks 655 in deformable outermost portion 617 of roll 616 are refilled as the roll 616 passes through liquid filled tank 650. Continuous operation of the embossing and supply rolls maintains a substantially steady state condition similar to that shown in FIG. 15 at the infeed to the nip formed between rolls 615 and 616.

Although FIG. 14 discloses the use of a roll of substantially flat film as a starting material, it is recognized that the process could be coupled directly to an extruder such that the incoming web of extruded material is fed directly into the nip formed between rolls 615 and 616. (This would, of course, eliminate the need for ancillary heating means 602 schematically shown in FIG. 14). However, it is generally preferred that the incoming web of extruded material be allowed to cool sufficiently to avoid sticking problems as the web passes through the nip formed between embossing rolls 615,616.

It is further recognized that while a forming structure generally similar to that shown in the process embodiment of FIGS. 12 and 13 is preferred for the process schematically illustrated in FIG. 14, the need for underlying layer 417 to be pervious to air is less pronounced in the process embodiment of FIG. 14. This is due to the fact that any air trapped in any capillary networks which may be present on the surface of roll 615 will tend to behave as a compressible fluid when opposed by the relatively high hydraulic pressures developed by the incompressible fluid present on the opposite surface of the film 610 as roll 616 undergoes deformation.

EXEMPLARY WEB EMBODIMENT PRODUCED VIA THE PROCESS OF FIG. 14

To demonstrate the efficacy of the process generally illustrated in FIG. 14, an exemplary "planar" microbubbled web of the present invention was produced. The starting material comprised a web 610 which was a blend polyethylene designated Ethyl Visqueen No. X-4242, as available from Ethyl Visqueen of Richmond, Va. The initial thickness of the web prior to processing was approximately 1 mil (0.001 inches). The outermost woven wire portion of the forming structure was comprised of a regularly spaced pattern of filaments having a diameter of approximately 5.5 mils (0.0055 inches). The filament density was about 80 filaments per lineal inch by about 80 filaments per lineal inch. The overall thickness of the outermost woven wire portion of the forming structure measured approximately 11 mils (0.011 inches). Immediately beneath the outermost woven wire portion of the forming structure there was provided a finer mesh woven wire back-up screen comprised of filaments having a diameter of approximately 1.6 mils (0.0016 inches) and a density of approximately 250 filaments per lineal inch by approximately 250 filaments per lineal inch. The overall thickness of the latter screen was approximately 3 mils (0.003 inches). The 80 mesh and the 250 mesh woven wire screens were mechanically held together in intimate contact with an underlying cylindrical support structure (not shown). The upper embossing roll 615 thus formed exhibited an outside diameter of approximately 8 inches and a width of approximately 6 inches. It was rotated at a peripheral speed of approximately 300 feet per minute.

The lower embossing roll 616 comprised a cylindrical steel roll 618 coated with approximately 0.75 inches of Shore A-50 durometer rubber 617. The rubber coating 617 had a multiplicity of regularly spaced, hexagonally shaped, blind capillary networks 655 about its periphery. The capillary networks had a density of approximately 50 per lineal inch by approximately 50 per lineal inch. Each capillary network had a maximum cross-sectional dimensions, as measured across the flats of the hexagon, of approximately 15 mils (i.e., 0.015 inches), and a sidewall length as measured along the side wall of the hexagon, of approximately 7.5 mils (i.e., 0.0075 inches), yielding a cross-sectional area of about 0.0002 square inches. The depth of the blind capillary networks was approximately 85 mils (0.085 inches). The outside diameter of roll 616 was approximately 8 inches, as measured in an undeformed condition, and its width was approximately 6 inches. The portion of roll 616 subject to deformation and pressure at the nip formed with roll 615 was about 1 inch, as measured peripherally along uppermost embossing roll 615. The lowermost embossing roll 616 exhibited a maximum deformation of about 95 mils (0.095 inches), as measured at the centerline connecting the axes of rotation of rolls 615 and 616. The deformation of roll 616 allowed the formation of a seal around the uppermost embossing roll 615 and the web 610, as generally shown in FIG. 15.

The deformable surface 617 of lowermost roll 616 was contacted by a fully submerged, smooth surfaced, metal pressure roll 675, as it entered water tank 650. The pressure roll 675 exhibited a diameter of 2½ inches. The contact pressure generated by roll 675 was sufficient to remove any air trapped in the blind capillary networks 655 contained on the surface 617 of lowermost roll 616. The temperature of the water 660 in tank 650 was approximately 195° F. The heated water 660 housed in tank 650 was picked up by the blind capillary networks 655 on the lowermost embossing roll 617. As the water filled, blind capillary networks 655 approached the embossing nip formed between rolls 615 and 616, additional water 660 was sprayed by a water nozzle 685 onto the surface of the blind capillary networks. The water spray contacted the lowermost embossing roll 616 at a point approximately ½ inch ahead of the nip. The temperature of the water employed in the spray was approximately 198° F.. The volume of water contained in the spray was sufficient to flood the nip and thereby compensate for any water lost by the blind capillary networks 655 during rotation of lowermost embossing roll 616.

The force $F_1$ applied between rolls 615 and 616 was between approximately 1,500 and 1,800 pounds. The water trapped in the seal between the uppermost and lowermost embossing rolls was forced against the lowermost surface of the web 610 under a contact pressure of approximately 285–300 psi, as measured using a pressure sensitive film such as Fuji Prescale Film, as available from Fuji Photo Film Company, Ltd. of Tokyo, Japan.

The resultant "planar" microbubbled web 610 exhibited a regularly repeating pattern of mushroom shaped surface aberrations 620, each having a highly thinned membrane 640 coincident with its point of maximum amplitude and continuously joined about its periphery to a relatively thicker base portion 630. The density of microbubbled surface aberrations 620 correspond to the density of the interstices in the outermost woven wire portion of the forming structure, i.e. approximately 80 microbubbled surface aberrations per lineal inch by approximately 80 microbubbled surface aberrations per lineal inch. The overall caliper of the resultant "planar" microbubbled web 610 was approximately 9 mils (0.009 inches), as measured under a low load condition of approximately 0.21 pounds/in$^2$ (95 grams/in$^2$). The microbubbled portions of the surface aberrations of the opaque web were substantially transparent. The exemplary web had a physical appearance generally similar to those illustrated in FIGS. 3, 4 and 13B.

MACROSCOPICALLY EXPANDED WEBS OF THE PRESENT INVENTION

The detailed description contained herein has to this point been confined to the production of microbubbled and/or microbubbled/microapertured webs which are substantially "planar", as that term has been defined herein. In many instances, it may be desirable to provide macroscopically expanded webs which exhibit patterns of microbubbled surface aberrations on all or a portion of their surface. In some instances, it may even be desirable to macroscopically aperture all or a portion of the surface of these webs to provide an ability to rapidly transmit fluids in combination with previously unachievable characteristics. Webs of the latter type may find particular utility as non-staining topsheets in products such as sanitary napkins.

Commonly assigned U.S. Pat. No. 4,609,518 issued to Curro et al. on Sept. 2, 1986 discloses multi-phase method and apparatus for providing macroscopically expanded polymeric webs exhibiting microscopic patterns of microapertured surface aberrations. The same basic approaches outlined in the aforementioned commonly assigned U.S. Patent to Curro et al. can be employed to provide macroscopic profiling and/or macroscopic aperturing of microbubbled webs of the present invention. Several possible web configurations are illustrated in cross-section in greatly enlarged form in Drawing FIGS. 16–21.

Figure 16:
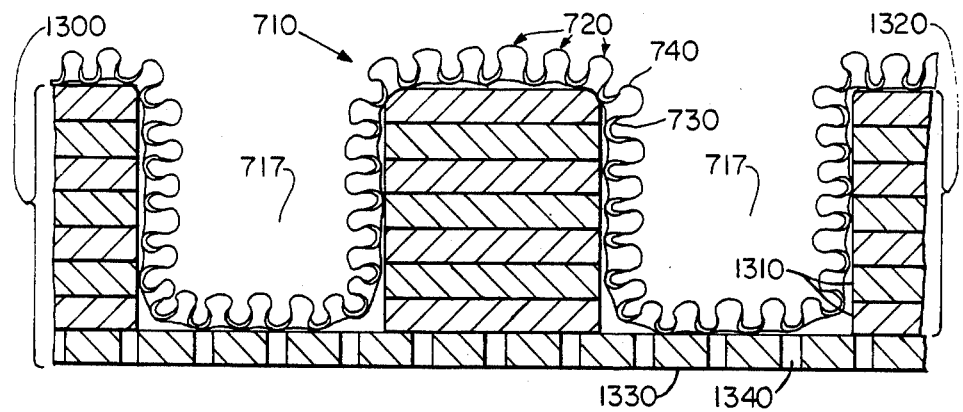
FIG. 16 is an enlarged, simplified cross-sectional illustration of a microbubbled web of the present invention which has been further subjected to macroscopic expansion to impart a three-dimensional profile subsequent to formation of the microbubbles, the microbubbled surface of said web being upwardly oriented relative to the macroscopically patterned forming structure on which the web is transformed, said web being shown prior to removal from said macroscopically patterned forming structure.

FIG. 16 is a simplified schematic representation of a substantially fluid-impervious, macroscopically expanded microbubbled web 710 which exhibits a pattern of unapertured macroscopic cross-section debossments 717, said web also exhibiting a continuous pattern of mushroom shaped surface aberrations 720, each exhibiting a relatively thin, upwardly oriented microbubbled portion 740 substantially coincident with its point of maximum amplitude and continuously secured about its periphery to a relatively thicker base portion 730 originating in the plane of the web.

The macroscopically expanded, microbubbled web 710 is shown prior to removal from the macroscopically patterned forming structure 1300 on which it was transformed from its substantially "planar" condition. (Note that the highly enlarged forming structure segments illustrated in FIG. 16–21 are shown in a substantially flat condition for simplicity. If actually employed in either of the process embodiments illustrated in FIGS. 12 or 14, these cross-sectional segments would be curvilinear in appearance.) Macroscopically patterned forming structure 1300 is preferably comprised of a multiplicity of relatively thin, identically apertured metal sheets 1310 which are bonded to one another generally in accordance with the teachings of commonly assigned U.S. Pat. No. 4,342,314 issued to Radel et al. to form a macroscopically patterned integral laminate portion 1320. Underlying and preferably bonded to the integral laminate portion 1320 is another layer 1330 containing a substantially continuous pattern of apertures 1340. The apertures 1340 are sized and spaced to permit air to pass through, yet provide support to the microbubbled web 710 in the areas coinciding with the end walls of the macroscopic cross-section debossments 717 to prevent rupture of the web in these areas.

The substantially "planar" microbubbled web is preferably debossed in the image of forming structure 1300 by contacting it with a high pressure liquid stream, as generally taught by commonly assigned U.S. Pat. No. 4,609,518 issued to Curro et al.

In the embodiment illustrated in FIG. 16, the microbubbled portions 740 of surface aberrations 720 are upwardly oriented during the macroscopic expansion process, i.e., they do not contact forming structure 1300.

Figure 20:
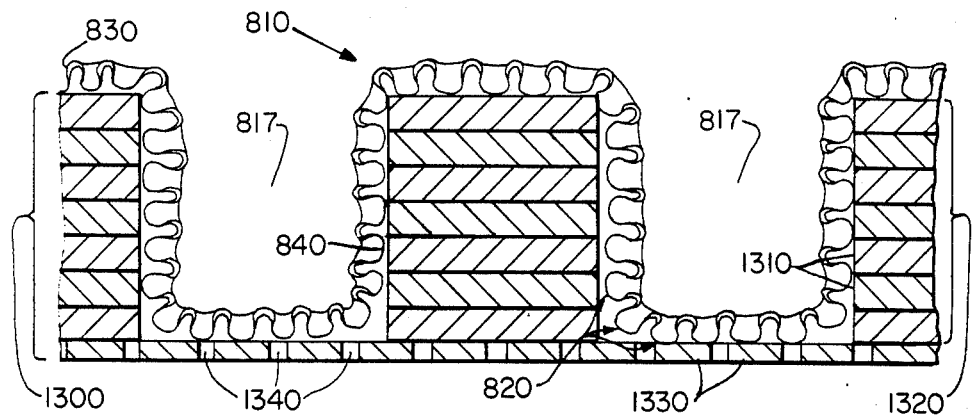
FIG. 20 is an enlarged, simplified cross-sectional illustration of a microbubbled, macroscopically expanded web generally similar to that shown in FIG. 16, the chief difference being that the web has its microbubbled surface downwardly oriented rather than upwardly oriented relative to the macroscopically patterned forming structure on which the web is transformed, said web being shown prior to removal from said macroscopically patterned forming structure.

FIG. 20 is a view of a web 810 generally similar to web 710 of FIG. 16, but illustrating the condition existing when the microbubbled portions 840 of the mushroom shaped surface aberrations 820 are downwardly oriented relative to the unapertured macroscopic cross-section debossments 817, i.e., they contact the macroscopically patterned forming structure 1300 on which the web was transformed from its substantially "planar" condition. As with web 710, the microbubbled portions 840 of the surface aberrations 820 are each continuously secured about their periphery to a relatively thicker base portion 830.

Webs of the type shown in either FIG. 16 or FIG. 20 may be created by subjecting an initially "planar" microbubbled web of the present invention to macroscopic expansion generally in accordance with the teachings of the aforementioned commonly assigned U.S. Pat. No. 4,609,518 to Curro et al.

Figure 17:
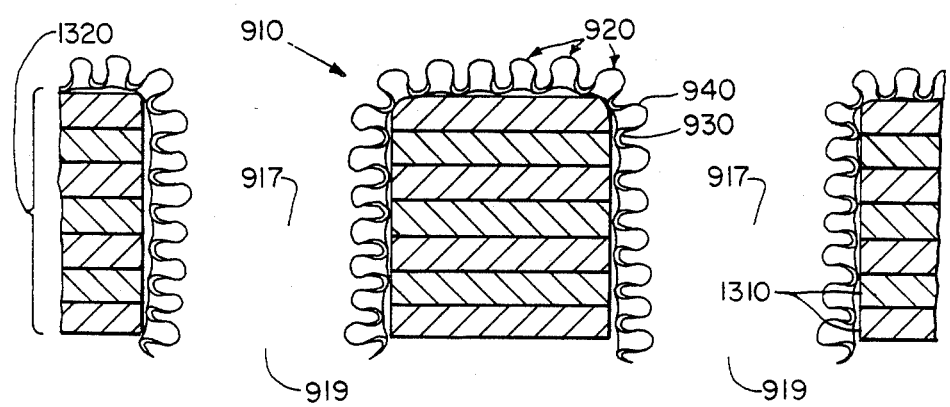
FIG. 17 is a view generally similar to that of FIG. 16, but illustrating a microbubbled web which has been both macroscopically expanded to impart a three-dimensional profile and macroscopically apertured subsequent to formation of the microbubbles, the microbubbled surface of said web also being upwardly oriented relative to the macroscopically patterned forming structure on which the web is transformed, said web being shown prior to removal from said macroscopically patterned forming structure.

Macroscopically expanded and macroscopically apertured microbubbled polymeric web 910 shown in FIG. 17 differs from macroscopically expanded microbubbled polymeric web 710 by virtue of the fact that the end walls of the macroscopic debossments 917 are macroscopically apertured at 919 to provide a high degree of fluid permeability. The upwardly oriented mushroom shaped surface aberrations 920 are otherwise identical to mushroom shaped surface aberrations 720, i.e., they exhibit a microbubbled portion 940 continuously secured about their periphery to a relatively thicker base portion 930. As can be seen in FIG. 17, the macroscopically patterned forming structure employed to macroscopically expand and macroscopically aperture web 910 comprises only the integral laminate portion 1320 of the forming structure 1300 shown in FIG. 16. Because the apertured layer 1330 is not present in this embodiment, the unsupported end walls of the macroscopic cross-section debossments 917 are ruptured by the high pressure liquid stream used to transform the web from its substantially "planar" condition.

Figure 21:
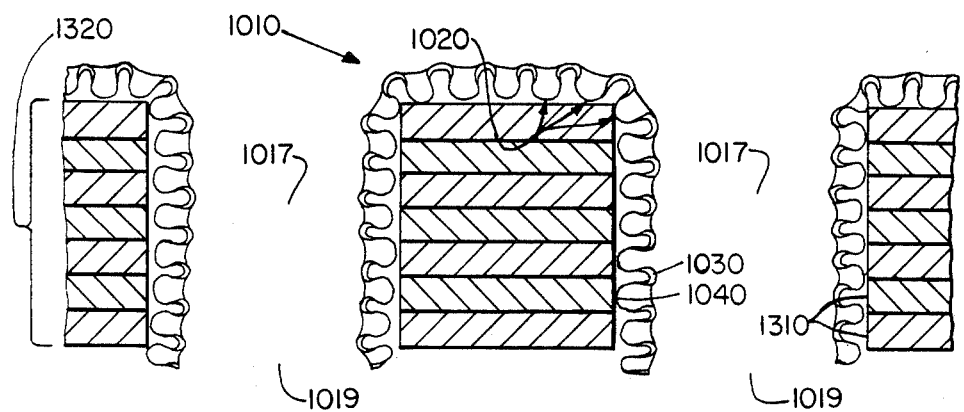
FIG. 21 is an enlarged, simplified cross-sectional illustration of a microbubbled, macroscopically expanded and macroscopically apertured web generally similar to that shown in FIG. 17, the chief difference being that the web has its microbubbled surface downwardly oriented rather than upwardly oriented relative to the macroscopically patterned forming structure on which the web is transformed, said web being shown prior to removal from said macroscopically patterned forming structure.

Macroscopically expanded and macroscopically apertured web 1010 shown in FIG. 21 differs from macroscopically expanded and macroscopically apertured web 910 shown in FIG. 17 only with respect to the downward orientation of the microbubbled portions 1040 of the surface aberrations 1020 relative to the macroscopic debossments 1017 and macroscopic apertures 1019, i.e., they contact the macroscopically patterned forming structure 1320 during the transformation process. Mushroom shaped surface aberrations 1020 are otherwise identical to mushroom shaped surface aberrations 920, i.e., they exhibit a microbubbled portion 1040 continuously secured about their periphery to a relatively thicker base portion 1030.

Figure 18:
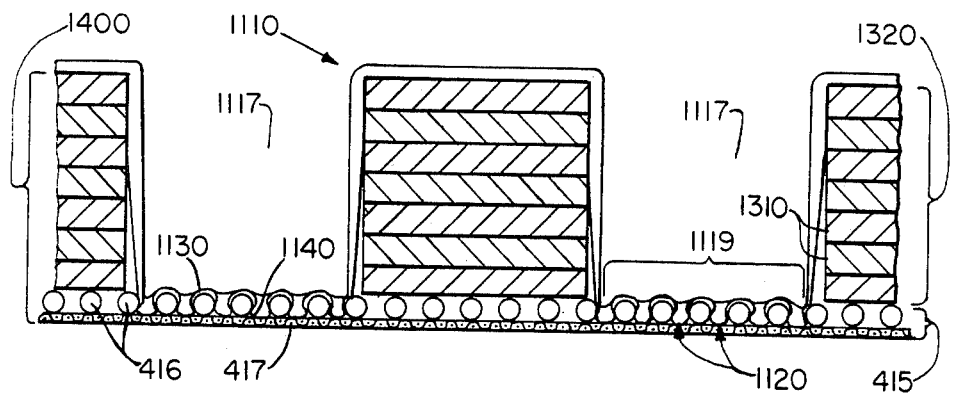
FIG. 18 is an enlarged, simplified cross-sectional illustration of another embodiment of a web of the present invention, said web having been macroscopically expanded to impart a three-dimensional profile and microbubbled only in the end walls of the macroscopic cross-section debossments formed in said web, the microbubbled surface of said web being downwardly oriented.

It is also possible in practicing the present invention to produce substantially fluid-impervious macroscopically expanded webs which limit the area of microbubbled surface aberrations to less than the entire surface of the web, e.g., to the endwalls of the macroscopic cross-section debossments and/or to the land areas, i.e., the non-debossed portions of the web. FIG. 18 is an example of such a web 1110 employing a pattern of substantially fluid-impervious macroscopic cross-section debossments 1117, each macroscopic cross-section debossment having a microbubbled endwall 1119. Such substantially fluid impervious macroscopically expanded webs permit much greater degrees of freedom in visual design while substantially maintaining the desired tactile response and noise reduction characteristics of microbubbled webs of the present invention.

In the illustrated web embodiment 1110, the microbubbled portions 1140, which are continuously secured about their periphery to relatively thicker base portions 1130 of the mushroom shaped surface aberrations 1120, are downwardly oriented relative to the macroscopically patterned forming structure 1400 shown in FIG. 18.

The macroscopically patterned, composite forming structure 1400 shown in FIG. 18 can, if desired, be comprised of a multiplicity of relatively thin, identically apertured metal sheets 1310 which are bonded to one another via a substantially dry bonding process, such as diffusion bonding, to form a macroscopically patterned integral laminate portion 1320 identical to that shown and described in conjunction with FIG. 17. Underlying and preferably bonded to the integral laminate 1320 is another finer scale laminate forming structure 415, which can, if desired, be identical to microbubble forming structure 415 shown in FIGS. 12 and 13.

A comparison of FIG. 13, which shows microbubble forming structure 415 in a greatly enlarged condition, with FIG. 18, which shows microbubble forming structure 415 enlarged to a much lesser degree, helps to illustrate the difference between "macroscopically expanded" and "planar" microbubbled webs of the present invention.

A macroscopically expanded, microbubbled web 1110 of the type shown in FIG. 18 can be produced utilizing a single stage high pressure liquid stream of the type generally illustrated in FIG. 12 when a macroscopically patterned composite forming structure 1400 is employed in lieu of the microbubble forming structure 415 shown by itself in Figures 12 and 13.

Alternatively, the web can be processed in two sequential forming phases, as generally disclosed in commonly assigned U.S. Pat. No. 4,609,518 issued to Curro et al. on Sept. 2, 1986 and incorporated herein by reference. In the latter case, the macroscopically expanded, microbubbled web 1110 can be produced by feeding a reheated polymeric web or by extruding a molten polymeric film directly onto a composite forming structure 1400 of the type shown in FIG. 18 while subjecting the film to vacuum to conform it to the macroscopic pattern of the forming structure. A second stage then follows in which a high pressure liquid stream is utilized to form surface aberrations 1120 having highly thinned microbubbles 1140 at their tips. Because of the geometry of the composite forming structure 1400, microbubbled surface aberrations 1120 are formed only in the endwalls of the debossments 1117.

While either a single phase or a multi-phase process may be utilized with forming structures of the type generally shown in FIG. 18, other considerations such as material type, degree of debossment, process costs, etc. may make one process more suitable than the other.

Figure 19:
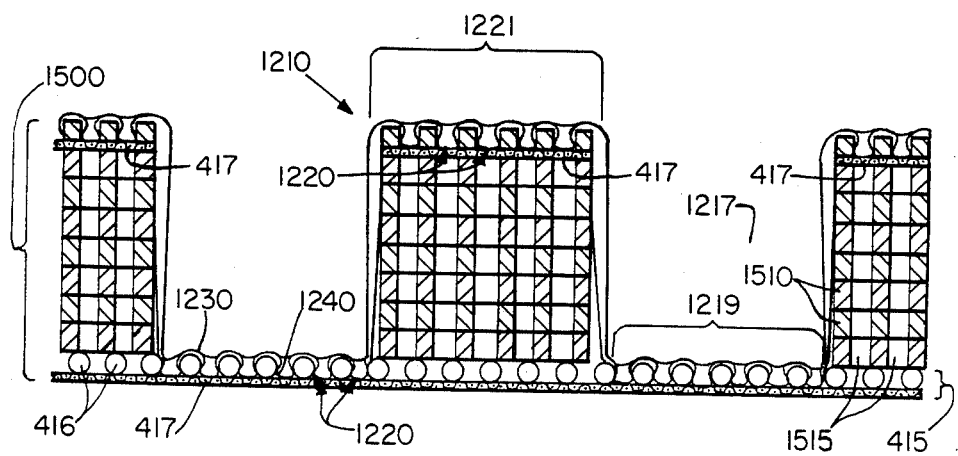
FIG. 19 is an enlarged, simplified cross-sectional view of a web of the present invention which has been macroscopically expanded to impart a three-dimensional profile and microbubbled both in its land areas and in the end walls of the macroscopic cross-section debossments formed in said web, the microbubbled surfaces of said web being downwardly oriented.

Web 1210 shown in FIG. 19 represents still another possible embodiment of a substantially fluid-impervious, macroscopically expanded, microbubbled web of the present invention. Web 1210 has been macroscopically expanded to provide a pattern of macroscopic debossments 1217 therein. The web exhibits both microbubbled land areas 1221 and microbubbled endwalls 1219 in the macroscopic cross-section debossments 1217. As can be seen from FIG. 19, the downwardly oriented microbubbled portions 1240 of the mushroom shaped surface aberrations 1220 in web 1210 are continuously secured about their periphery to a relatively thicker base portion 1230 and are oriented in the same direction as the downwardly oriented microbubbled portions 1140 of the mushroom shaped surface aberrations 1120 in the microbubbled endwalls 1119 of web embodiment 1110 shown in FIG. 18.

The composite macroscopically-patterned threedimensional forming structure 1500 shown in FIG. 19 preferably comprises a multiplicity of thin metal sheets 1510 exhibiting coinciding patterns of macroscopic cross-section apertures which, when stacked upon one another, form capillary networks corresponding to macroscopic cross-section debossments 1217. The underlying microbubble forming structure 415 can, if desired, be identical to the one utilized in the forming structure embodiment 1400 shown in FIG. 18. The multiplicity of capillary networks corresponding to microbubbled surface aberrations 1220 in the non-debossed land areas 1221 of the web 1210, are provided by the pattern of the smaller apertures 1515 in the thin metal sheets 1510. These smaller apertures also form continuous passageways interconnecting the uppermost and lowermost surfaces of the entire stack of metal sheets 1510. A porous support layer, which can be identical to layer 417, is preferably provided near the uppermost surface of the forming structure to provide support to the microbubbles to be formed in the land areas 1221 of the film. Depending upon the size of the apertures 1515 and the thickness of the sheets 1510, the porous layer 417 is frequently positioned beneath the first or second apertured metal sheet 1510 in the stack. In the embodiment illustrated in FIG. 19, it is shown immediately beneath the first such sheet 1510. Thus the surface aberrations 1220 in the non-debossed land areas 1221 of web 1210 correspond to the apertures 1515 in the uppermost thin metal sheet 1510.

Because the layer 417 is porous, air which would otherwise be trapped by the web in the capillary networks comprising apertures 1515 in uppermost metal sheet 1510 is allowed to vent through the continuous passageways formed by the coinciding apertures 1515 in the underlying stack of metal sheets 1510. This permits formation of microbubbled surface aberrations 1220 in the land areas 1221 of the web without compression of the air contained in the capillary networks comprising apertures 1515 in uppermost metal sheet 1510.

As will be appreciated, the exact configuration of the composite macroscopically patterned three-dimensional forming structure 1500 is only intended to be exemplary. Many variations of construction are possible, depending upon whether microbubbled surface aberrations 1220 are desired only in the land areas 1221, only in the end walls 1219 of the macroscopic cross-section debossments 1217, or both.

The mushroom shaped surface aberrations 1220 in the land areas 1221 of macroscopically expanded web 1210, the macroscopic cross-section debossments 1217 and the mushroom shaped surface aberrations 1220 in the end walls 1219 of the macroscopic cross-section debossments may be formed by utilizing a single stage high pressure liquid stream of the type generally illustrated in FIG. 12 in conjunction with a composite macroscopically patterned three-dimensional forming structure 1500 of the type generally shown in FIG. 19.

Should it be desirable to provide microbubbled surface aberrations 1220 only in the non-debossed land areas 1221 of the macrosopically expanded web 1210, this could be achieved in stages. A substantially planar polymeric web could first be subjected to vacuum while in a heated condition to cause it to conform to the macroscopic profile of the composite forming structure 1500. The vacuum employed should be insufficient to form microbubbled surface aberrations 1220 in either the land areas 1221 of the web or the end walls 1219 of the macroscopic cross-section debossments 1217. The macroscopically expanded web containing macroscopic cross-section debossments 1217 could then be passed through a hydraulic nip of the type generally illustrated in FIG. 14 prior to removal from the macroscopically patterned forming structure 1500. If desired, the web could be maintained at an elevated temperature or reheated to soften it prior to passing it through the aforementioned hydraulic nip to provide improved conformability of the film to the fine-scale pattern of capillary networks comprising apertures 1515 in uppermost metal sheet 1510. The resultant web would exhibit macroscopic cross-section debossments 1217 and microbubbled surface aberrations 1220 only in its non-debossed land areas 1221.

From the description contained herein, it is clear that webs of the present invention provide a unique combination of characteristics previously unobtainable in a single layer, substantially fluid-impervious polymeric web, i.e., cloth-like visual and tactile impression, softness, conformability, and little or no "noise" when subjected to movement, particularly when used as a substantially fluid-impervious backsheet in a disposable absorbent bandage worn under the clothing.

While the present invention has been described primarily in the context of a backsheet for a disposable absorbent bandage, it is recognized that the present invention may also be practiced to advantage in many other applications and environments. It will be obvious to those skilled in the art that various changes and modifications can be made without departing from the spirit and scope of the invention, and it is intended to cover in the appended claims all such modifications that are within the scope of this invention.

What is claimed is:

1. A continuous method for forming a substantially fluid-impervious polymeric web exhibiting a pattern of discrete microbubbled surface aberrations from an initially flat web, said microbubbled web exhibiting very low levels of noise when subjected to movement, said method comprising the steps of:
    (a) continuously bringing said substantially fluid-impervious flat polymeric web into contacting relation with a continuous, moving forming member exhibiting a first pattern of apertures substantially corresponding to said surface aberrations and extending from the outermost to the innermost surface of said forming member;
    (b) applying a substantially unconstrained liquid stream, which is substantially stationary in the direction of travel of said moving flat polymeric web, substantially uniformly to the exposed surface of said moving flat polymeric web while said web is supported on said forming member, said substantially unconstrained liquid stream having sufficient force and mass flux to cause said moving flat polymeric web to be permanently deformed toward said forming member upon contact therebetween, such that said polymeric web substantially conforms to the image of said first pattern of apertures in said forming member to provide a pattern of surface aberrations in said web, each of said surface aberrations having a base portion and an end portion;

(c) supporting the end portions of said surface aberrations formed in said web on a porous support member secured in underlying relation to the innermost surface of said forming member while said surface aberrations remain subject to the influence of said substantially stationary liquid stream, said porous support member exhibiting a second pattern of apertures smaller in size and higher in frequency than the apertures in said forming member, whereby the end portion of each of said surface aberrations is highly thinned without being ruptured by said liquid stream to form a microbubble substantially coinciding with the point of maximum amplitude of the surface aberration to which it is continuously joined about its periphery, said microbubble comprising a highly flexible, substantially fluid-impervious, continuous membrane which is very much thinner than the base portion of said surface aberration, said microbubble further exhibiting a maximum internal cross-sectional area, as measured in its fully expanded condition in a first plane oriented perpendicular to the amplitude of said surface aberration, which is greater than the minimum internal cross-sectional area of said relatively thicker base portion to which it is continuously secured about its periphery, as measured in a second plane oriented parallel to said first plane; and (d) removing said substantially fluid-impervious microbubbled polymeric web from said forming member.

2. The method of claim 1, wherein the density of said microbubbled surface aberrations formed in said web is at least about 2,500 per square inch.

3. The method of claim 1, wherein said liquid in said unconstrained liquid stream comprises water and said water in said unconstrained liquid stream is preheated.

4. The method of claim 3, wherein said water is preheated to a temperature between about 40° C. and about 90° C.

5. The method of claim 4, wherein the temperature of said web of material is controlled such that it remains in a substantially solid state throughout said process, thereby substantially preserving the physical properties and thermo-mechanical history of the incoming web of polymeric material.

6. The method of claim 5 including the step of applying a spray of cooling liquid to the exposed surface of said microbubbled web prior to removing said web from said forming member to prevent roping of said web due to the effects of tension.

7. The method of claim 6, including the step of drawing a cooling medium through said continuous, moving forming member after said microbubbled web has been removed therefrom and prior to said continuous forming member being contacted by said incoming polymeric web.

8. The method of claim 7, wherein said cooling medium is comprised substantially of air.

9. The method of claim 8, wherein said forming member comprises the outermost surface of a cylindrical forming drum.

10. The method of claim 8, wherein said forming member comprises the outermost surface of an endless belt.

11. The method of claim 2 wherein the maximum center-to-center distance between adjacent surface aberrations formed in said web is about 25 mils (0.025 inches).

12. The method of claim 11, wherein said first pattern of apertures in said forming member is regularly repeating.

13. The method of claim 12, wherein said first pattern of apertures in said forming member is regularly spaced.

14. The method of claim 13, wherein said porous support member supporting the end portions of said surface aberrations while they are subject to the influence of said substantially stationary liquid stream comprises a woven wire mesh having a filament density of at least about 165 filaments per lineal inch by about 800 filaments per lineal inch.

15. The method of claim 1, wherein said liquid stream is applied to the exposed surface of said polymeric web from high pressure spray nozzles, liquid being supplied to said spray nozzles at a pressure of at least about 350 N/cm$^2$ (500 PSIG).

16. The method of claim 1, wherein said liquid stream is applied to said exposed surface of said polymeric web from high pressure spray nozzles, liquid being supplied to said spray nozzles at a pressure of at least about 700 N/cm$^2$ (1000 PSIG).

17. The method of claim 1, wherein said incoming polymeric web exhibits a low degree of molecular orientation, a low yield strength, a high elongation characteristic and a tendency to strain harden when subjected to elongation.

18. A continuous method for forming a macroscopically patterned, three-dimensional, substantially fluid-impervious polymeric web exhibiting a pattern of discrete microbubbled surface aberrations from an initially flat web, said microbubbled web exhibiting very low levels of noise when subjected to movement, said method comprising the steps of:

(a) continuously bringing said substantially fluid-impervious flat polymeric web into contacting relation with a first continuous, moving forming member exhibiting a first pattern of apertures substantially corresponding to said surface aberrations and extending from the outermost to the innermost surface of said forming member;

(b) applying a first substantially unconstrained liquid stream, which is substantially stationary in the direction of travel of said moving flat polymeric web, substantially uniformly to the exposed surface of said moving flat polymeric web while said web is supported on said forming member, said substantially unconstrained liquid stream having sufficient force and mass flux to cause said moving flat polymeric web to be permanently deformed toward said forming member upon contact therebetween, such that said polymeric web substantially conforms to the image of said first pattern of apertures in said forming member to provide a pattern of surface aberrations in said web, each of said surface aberrations having a base portion and an end portion;

(c) supporting the end portions of said surface aberrations formed in said web on a porous support member secured in underlying relation to the innermost surface of said forming member while said surface aberrations remain subject to the influence of said substantially stationary liquid stream, said porous support member exhibiting a second pattern of apertures smaller in size and higher in frequency than the apertures in said forming member, whereby the end portion of each of said surface aberrations is highly thinned without being ruptured by said liquid stream to form a microbubble substantially coinciding with the point of maximum amplitude of the surface aberration to which it is continuously joined about its periphery, said microbubble comprising a highly flexible, substantially fluid-impervious, continuous membrane which is very much thinner than the base portion of said surface aberration, said microbubble further exhibiting a maximum internal cross-sectional area, as measured in its fully expanded condition in a first plane oriented perpendicular to the amplitude of said surface aberration, which is greater than the minimum internal cross-sectional area of said relatively thicker base portion to which it is continuously secured about its periphery, as measured in a second plane oriented parallel to said first plane;

(d) removing said substantially fluid-impervious microbubbled polymeric web from said forming member;

(e) supporting said moving, substantially fluid-impervious microbubbled web on a second, macroscopically pattern, moving, three-dimensional forming member;

(f) subjecting said web to a second substantially unconstrained liquid stream having sufficient force and mass flux to cause said moving microbubbled polymeric web to be permanently deformed substantially in the image of said second macroscopically patterned, three-dimensional forming member; and (g) removing said macroscopically patterned, three-dimensional, substantially fluid-impervious microbubbled web from said second forming member.

19. The method of claim 18, including the step of macroscopically aperturing said macroscopically expanded, three-dimensional web at predetermined points along its surface to render said web pervious to the transmission of fluid at said predetermined points.

20. The method of claim 18 or Claim 19, wherein the macrobubbled portions of said surface aberrations in said web are oriented toward said second liquid stream when said microbubbled web is being macroscopically expanded in the image of said second forming member.

21. A continuous method for forming a macroscopically expanded, three-dimensional, substantially fluid-impervious polymeric web from an initially flat web, said macroscopically expanded, three-dimensional web exhibiting a pattern of macroscopic cross-section debossments, said macroscopically expanded, three-dimensional web further exhibiting a pattern of discrete microbubbled surface aberrations only in its non-debossed portions, said macroscopically expanded, three-dimensional web exhibiting very low levels of noise when subjected to movement, said method comprising the steps of:

(a) continuously bringing said substantially fluid-impervious flat polymeric web into contacting relation with a continuous, moving forming member exhibiting a first pattern of apertures corresponding to said surface aberrations and a second pattern of macroscopic cross-section apertures corresponding to said macroscopic cross-section debossments;

(b) applying a substantially unconstrained liquid stream, which is substantially stationary in the direction of travel of said moving flat polymeric web, substantially uniformly to the exposed surface of said moving flat polymeric web while said web is supported on said forming member, said substantially unconstrained liquid stream having sufficient force and mass flux to cause said moving flat polymeric web to be permanently deformed toward said forming member upon contact therebetween, such that said polymeric web substantially conforms to the image of said first pattern of apertures in said forming member to provide a pattern of surface aberrations, each having a base portion and an end portion, and to said second pattern of macroscopic cross-section apertures to provide a pattern of macroscopic cross-section debossments in said web;

(c) supporting the end portions of said surface aberrations formed in said web on a porous support member secured in underlying relation to the portions of said forming member exhibiting said first pattern of apertures while said surface aberrations remain subject to the influence of said substantially stationary liquid stream, said porous support member exhibiting a third pattern of apertures smaller in size and higher in frequency than said first pattern of apertures in said forming member, whereby the end portion of each of said surface aberrations is highly thinned without being ruptured by said liquid stream to form a microbubble substantially coinciding with the point of maximum amplitude of the surface aberration to which it is continuously joined about its periphery, said microbubble comprising a highly flexible, substantially fluid-impervious, continuous membrane which is very much thinner than the base portion of said surface aberration, said microbubble further exhibiting a maximum internal cross-sectional area, as measured in its fully expanded condition in a first plane oriented perpendicular to the amplitude of said surface aberration, which is greater than the minimum internal cross-sectional area of said relatively thicker base portion to which it is continuously secured about its periphery, as measured in a second plane oriented parallel to said first plane; and (d) removing said macroscopically expanded, three-dimensional polymeric web exhibiting said pattern of macroscopic cross-section debossments and said pattern of discrete microbubbled surface aberrations from said forming member.

22. A continuous method for forming a macroscopically expanded, three-dimensional, substantially fluid-impervious polymeric web from an initially flat web, said macroscopically expanded, three-dimensional web exhibiting a pattern of macroscopic cross-section debossments, each of said macroscopic cross-section debossments comprising a substantially fluid-impervious end wall portion joined to the non-debossed portions of said web by a continuous side wall, said macroscopically expanded, three-dimensional web further exhibiting a pattern of discrete microbubbled surface aberrations only in said end wall portions of said macroscopic cross-section debossments, said macroscopically expanded, three-dimensioanl web exhibiting very low levels of noise when subjected to movement, said method comprising the steps of:

(a) continuously bringing said substantially fluid-impervious flat polymeric web into contacting relation with a continuous, moving forming member exhibiting a first pattern of macroscopic cross-section apertures corresponding to said macroscopic cross-section debossments in its outermost surface and a second pattern of smaller apertures substantially corresponding to said surface aberrations underlying said macroscopic cross-section apertures;

(b) applying a substantially unconstrained liquid stream which is substantially stationary in the direction of travel of said moving flat polymeric web, substantially uniformly to the exposed surface of said moving flat polymeric web while said web is supported on said forming member, said substantially unconstrained liquid stream having sufficient force and mass flux to cause said moving flat polymeric web to be permanently deformed toward said forming member upon contact therebetween, such that said polymeric web substantially conforms to the image of said first pattern of macroscopic cross-section apertures to provide a pattern of macroscopic cross-section debossments in said web and to said second pattern of smaller apertures underlying said macroscopic cross-section apertures in said forming member to provide a pattern of surface aberrations, each having a base portion and an end portion only in the end wall portions of said macroscopic cross-section debossments of said web;

(c) supporting the end portions of said surface aberrations formed in said end wall portions of said macroscopic cross-section debossments on a porous support member secured in underlying relation to the portions of said forming member exhibiting said second pattern of apertures while said surface aberrations remain subject to the influence of said substantially stationary liquid stream, said porous support member exhibiting a third pattern of apertures smaller in size and higher in frequency than said second pattern of apertures in said forming member, whereby the end portion of each of said surface aberrations is highly thinned without being ruptured by said liquid stream to form a microbubble substantially coinciding with the point of maximum amplitude of the surface aberration to which it is continuously joined about its periphery, said microbubble comprising a highly flexible, substantially fluid-impervious, continuous membrane which is very much thinner than the base portion of said surface aberration, said microbubble further exhibiting a maximum internal cross-sectional area, as measured in its fully expanded condition in a first plane oriented perpendicular to the amplitude of said surface aberration, which is greater than the minimum internal cross-sectional area of said relatively thicker base portion to which it is continuously secured about its periphery, as measured in a second plane oriented parallel to said first plane; and (d) removing said macroscopically expanded, three-dimensional, substantially fluid-impervious polymeric web exhibiting said pattern of macroscopic cross-section debossments and said pattern of discrete microbubbled surface aberrations from said forming member.

23. A continuous method for forming a macroscopically expanded, three-dimensional, substantially fluid-impervious polymeric web from an initially flat web, said macroscopically expanded, three-dimensional web exhibiting a pattern of macroscopic cross-section debossments, each of said macroscopic cross-section debossments comprising a substantially fluid-impervious end wall portion joined to the non-debossed portions of said web by a continuous side wall, said macroscopically expanded, three-dimensional web further exhibiting a pattern of discrete microbubbled surface aberrations only in said end wall portions of said macroscopic cross-section debossments, said non-debossed portions of said web, said macroscopically expanded, three-dimensional web exhibiting very low levels of noise when subjected to movement, said method comprising the steps of:

(a) continuously bringing said substantially fluid-impervious flat polymeric web into contacting relation with a continuous, moving forming member exhibiting a first pattern of macroscopic cross-section apertures corresponding to said macroscopic cross-section debossments in its outermost surface and a second pattern of smaller apertures substantially corresponding to said surface aberrations in the non-debossed portions of said web as well as in the end walls of said macroscopic cross-section debossments;

(b) applying a substantially unconstrained liquid stream, which is substantially stationary in the direction of travel of said moving flat polymeric web, substantially uniformly to the exposed surface of said moving flat polymeric web while said web is supported on said forming member, said substantially unconstrained liquid stream having sufficient force and mass flux to cause said moving flat polymeric web to be permanently deformed toward said forming member upon contact therebetween, such that said polymeric web substantially conforms to the image of said first pattern of macroscopic cross-section apertures to provide a pattern of macroscopic cross-section debossments in said web and to said second pattern of smaller apertures in said forming member to provide a pattern of surface aberrations, each having a base portion and an end portion;

(c) supporting the end portions of said surface aberrations formed in said web on a porous support member secured in underlying relation to those portions of said forming member exhibiting said second pattern of apertures while said surface aberrations remain subject to the influence of said substantially stationary liquid stream, said porous support member exhibiting a third pattern of apertures smaller in size and higher in frequency than said second pattern of apertures in said forming member, whereby the end portion of each of said surface aberrations is highly thinned without being ruptured by said liquid stream to form a microbubble substantially coinciding with the point of maximum amplitude of the surface aberration to which it is continuously joined about its periphery, said microbubble comprising a highly flexible, substantially fluid-impervious, continuous membrane which is very much thinner than the base portion of said surface aberration, said microbubble further exhibiting a maximum internal cross-sectional area, as measured in its fully expanded condition in a first plane oriented perpendicular to the amplitude of said surface aberration, which is greater than the minimum internal cross-sectional area of said relatively thicker base portion to which it is continuously secured about its periphery, as measured in a second planeoriented parallel to said first plane; and (d) removing said macroscopically expanded, three-dimensional, substantially fluid-impervious polymeric web exhibiting said pattern of macroscopic cross-section debossments and said pattern of discrete microbubbled surface aberrations from said forming member.

24. The method of claim 21, claim 22 or claim 23, wherein the density of said microbubbled surface aberrations formed in said web is at least about 2,500 per square inch and the maximum center-to-center distance between adjacent surface aberrations is about 25 mils (0.025 inches).

25. The method of claim 21, claim 22 or claim 23, wherein said liquid in said unconstrained liquid stream comprises water and said water in said unconstrained liquid stream is preheated.

26. The method of claim 25, wherein said water is preheated to a temperature between about 40° C. and about 90° C.

27. The method of claim 26, wherein the temperature of said web of material is controlled such that it remains in a substantially solid state throughout said process, thereby preserving the physical properties and thermo-mechanical history of said substantially planar web of polymeric material.

28. The method of claim 27, including the step of applying a spray of cooling liquid to the exposed surface of said microbubbled web prior to removing said web from said forming member to prevent roping of said web due to the effects of tension.

29. The method of claim 28, including the step of drawing a cooling medium through said continuous, moving forming member after said microbubbled web has been removed therefrom and prior to said continuous forming member being contacted by said incoming polymeric web.

30. The method of claim 29, wherein said cooling medium is comprised substantially of air.

31. The method of claim 21, claim 22 or claim 23, wherein said porous support member supporting the end portions of said surface aberrations while they are subject to the influence of said substantially stationary liquid stream comprises a woven wire mesh having a filament density of at least about 165 filaments per lineal inch by about 800 filaments per lineal inch.

32. The method of claim 21, claim 22 or claim 23, wherein said liquid stream is applied to the exposed surface of said polymeric web from high pressure spray nozzles, liquid being supplied to said spray nozzles at a pressure of at least about 350 N/cm$^2$ (500 PSIG).

33. The method of claim 21, wherein said substantially unconstrained liquid stream has sufficient force and mass flux to rupture said end wall portions of said macroscopic cross-section debossments to form macroscopic cross-section apertures in said debossments, thereby rendering those portions of said web containing said macroscopic cross-section apertures pervious to the transmission of fluid.

34. An apparatus for continuously forming a substantially fluid-impervious microbubbled polymeric web from an initially flat web, said microbubbled web exhibiting very low levels of noise when subjected to movement, said apparatus comprising:

(a) a continuous forming member exhibiting a first pattern of apertures substantially corresponding to said surface aberrations and extending from the outermost to the innermost surface of said forming member;

(b) drive means for continuously moving said continuous forming member;

(c) means for continuously bringing said substantially fluid-impervious flat polymeric web in contacting relation with said moving forming member;

(d) means for applying a substantially unconstrained liquid stream, which is substantially stationary in the direction of travel of said moving flat polymeric web, substantially uniformly to the exposed surface of said moving flat polymeric web while said web is supported on said forming member, said substantially unconstrained liquid stream having sufficient force and mass flux to cause said moving flat polymeric web to be permanently deformed toward said forming member upon contact therebetween, such that said polymeric web substantially conforms to the image of said first pattern of apertures in said forming member to provide a pattern of surface aberrations in said web, each of said surface aberrations having a base portion and an end portion;

(e) a porous support member for supporting the end portions of said surface aberrations formed in said web while said surface aberrations remain subject to said substantially stationary liquid stream secured in underlying relation to the innermost surface of said forming member, said porous support member exhibiting a second pattern of apertures smaller in size and higher in frequency that the apertures in said forming member, whereby the end portion of each of said surface aberrations is highly thinned without being ruptured by said liquid stream to form a microbubble substantially coinciding with the point of maximum amplitude of the surface aberration to which it is continuously joined about its periphery, said microbubble comprising a highly flexible, substantially fluid-impervious, continuous membrane which is very much thinner than the base portion of said surface aberration, said microbubble further exhibiting a maximum internal cross-sectional area, as measured in its fully expanded condition in a first plane oriented perpendicular to the amplitude of said surface aberration, which is greater than the minimum internal cross-sectional area of said relatively thicker base portion to which it is continuously secured about its periphery, as measured in a second plane oriented parallel to said first plane; and (f) means for removing said substantially fluid-impervious microbubbled polymeric web from said forming member.

35. The apparatus of claim 34, wherein the density of apertures in said first pattern in said forming member is at least about 2,500 per square inch and the maximum center-to-center distance between adjacent apertures is about 25 miles (0.025 inches).

36. The apparatus of claim 34, including means for preheating said liquid in said unconstrained liquid stream.

37. The apparatus of claim 34 including the means for applying a spray of cooling liquid to the exposed surface of said microbubbled web prior to removing said web from said forming member to prevent roping of said web due to the effects of tension.

38. The apparatus of claim 37, including means for drawing a cooling medium through said continuous, moving forming member after said microbubbled web has been removed therefrom and prior to said continuous forming member being contacted by said incoming polymeric web.

39. The apparatus of claim 35, wherein said porous support member supporting the end portions of said surface aberrations while they are subject to the influence of said substantially stationary liquid stream comprises a woven wire mesh having a filament density of at least about 165 filaments per lineal inch by about 800 filaments per lineal inch.

40. The apparatus of claim 34, wherein said means for applying said substantially unconstrained liquid stream to the exposed surface of said polymeric web comprises high pressure spray nozzles.

41. The apparatus of claim 35, wherein said forming member further exhibits a second pattern of macroscopic cross-section apertures for macroscopically expanding said web in the three-dimensional image of said forming member.

42. The apparatus of claim 41, including means for macroscopically aperturing said macroscopically expanded, three-dimensional web at predetermined points along its surface to render said web pervious to the transmission of fluid at said predetermined points prior to removal of said web from said forming member.

* * * * *

UNITED STATES PATENT AND TRADEMARK OFFICE
CERTIFICATE OF CORRECTION

PATENT NO. : 4,778,644

DATED : October 18, 1988

INVENTOR(S) : JOHN J. CURRO, DONALD L. GERTH, WILLIAM I. MULLANE, JR.

It is certified that error appears in the above-identified patent and that said Letters Patent is hereby corrected as shown below:

Column 3, line 15, "individualy" should read -- individually --.

Column 5, line 30, "4,484,835" should read -- 3,484,835 --.

Column 9, line 16, "aformentioned" should read -- aforementioned --.

Column 10, line 52, "fluidimpervious" should read -- fluid-impervious --.

Column 12, line 65, "transmision" should read -- transmission --.

Column 17, line 61, "microapertures" should read -- microapertured --.

Column 21, line 3, "an" should read -- any --.

Column 27, line 48, "prefered" should read -- preferred --.

Column 27, line 63, "thereby" should read -- hereby --.

Column 29, line 61, after "519" insert -- in --.

Column 32, line 50, "17" should read -- 417 --.

Column 33, line 35, "network" should read -- networks --.

Column 35, line 58, "correspond" should read -- corresponded --.

Column 36, line 48, "FIG." should read -- FIGS. --.

Column 39, lines 14 and 15, "threedimensional" should read -- three-dimensional --.

UNITED STATES PATENT AND TRADEMARK OFFICE
CERTIFICATE OF CORRECTION

PATENT NO. : 4,778,644

DATED : October 18, 1988

INVENTOR(S) : JOHN J. CURRO, DONALD L. GERTH, WILLIAM I. MULLANE, JR.

It is certified that error appears in the above-identified patent and that said Letters Patent is hereby corrected as shown below:

Column 43, line 33, "pattern" should read -- patterned --.

Column 43, line 53, "macrobubbled" should read -- microbubbled --.

Column 47, lines 11 and 12, "planeoriented" should read -- plane oriented --.

Column 48, line 41, "that" should read -- than --.

Column 48, line 68, "miles" should read -- mils --.

Signed and Sealed this

Twenty-first Day of March, 1989

Attest:

DONALD J. QUIGG

Attesting Officer

Commissioner of Patents and Trademarks